(12) United States Patent
Davey et al.

(10) Patent No.: US 10,357,538 B2
(45) Date of Patent: Jul. 23, 2019

(54) VACCINES FOR THE TREATMENT OF CANCER AND COMPOSITIONS FOR ENHANCING VACCINE EFFICACY

(71) Applicant: Northern Sydney Local Health District, a body corporate, St. Leonards (AU)

(72) Inventors: Ross Arthur Davey, Willoughby (AU); Christopher John Weir, Frenchs Forest (AU)

(73) Assignee: NORTHERN SYDNEY LOCAL HEALTH DISTRICT, St. Leonards (AU)

(*) Notice: Subject to any disclaimer, the term of this patent is extended or adjusted under 35 U.S.C. 154(b) by 0 days.

(21) Appl. No.: 14/655,088

(22) PCT Filed: Dec. 24, 2013

(86) PCT No.: PCT/AU2013/001523
§ 371 (c)(1),
(2) Date: Jun. 24, 2015

(87) PCT Pub. No.: WO2014/100857
PCT Pub. Date: Jul. 3, 2014

(65) Prior Publication Data
US 2015/0343040 A1    Dec. 3, 2015

(30) Foreign Application Priority Data

Dec. 24, 2012 (AU) ................ 2012905667
Dec. 24, 2012 (AU) ................ 2012905669
Apr. 11, 2013 (AU) ................ 2013203806
Sep. 18, 2013 (AU) ................ 2013903592

(51) Int. Cl.
| | |
|---|---|
| *A61K 38/16* | (2006.01) |
| *A61K 38/17* | (2006.01) |
| *A61K 39/00* | (2006.01) |
| *A61K 39/09* | (2006.01) |
| *A61K 39/39* | (2006.01) |

(52) U.S. Cl.
CPC ........ *A61K 38/1703* (2013.01); *A61K 38/164* (2013.01); *A61K 39/0011* (2013.01); *A61K 39/092* (2013.01); *A61K 39/39* (2013.01); *A61K 2039/515* (2013.01); *A61K 2039/5152* (2013.01); *A61K 2039/54* (2013.01); *A61K 2039/545* (2013.01); *A61K 2039/55516* (2013.01); *A61K 2039/55588* (2013.01); *A61K 2039/585* (2013.01); *A61K 2039/6006* (2013.01); *A61K 2039/70* (2013.01)

(58) Field of Classification Search
CPC ................................................ B01D 15/3823
See application file for complete search history.

(56) References Cited

U.S. PATENT DOCUMENTS

| | | | |
|---|---|---|---|
| 5,030,621 A | 7/1991 | Bystryn | |
| 6,372,223 B1 | 4/2002 | Kistner et al. | |
| 7,029,678 B2 | 4/2006 | Momin et al. | |
| 2003/0105000 A1* | 6/2003 | Pero ............... | A61K 38/06 514/19.3 |
| 2011/0027311 A1 | 2/2011 | Deng et al. | |

FOREIGN PATENT DOCUMENTS

| | | | |
|---|---|---|---|
| CN | 1887296 | 1/2007 | |
| CN | 1887296 B * | 5/2011 | ............. A61K 39/00 |
| EP | 0399843 B1 | 7/1994 | |
| EP | 1216053 B1 | 11/2005 | |
| JP | S62-221636 | 9/1987 | |
| WO | 1999/015199 A1 | 4/1999 | |
| WO | 2000/35950 A2 | 6/2000 | |
| WO | 200501480 A1 | 1/2005 | |
| WO | 2005/020936 A2 | 3/2005 | |
| WO | 2005/093044 A1 | 10/2005 | |
| WO | 2007/006939 A2 | 1/2007 | |
| WO | 2013/040649 A1 | 3/2013 | |

OTHER PUBLICATIONS

Cleland W. W. (Biochemistry Apr. 1964 3(4): 1964).*
Bacterial lectin (https://www.ncbi.nlm.nih.gov/protein/?term=bacterial%20lectin downloaded, Oct. 14, 2016).*
Adhesin (https://www.ncbi.nlm.nih.gov/protein/?term=adhesin, downloaded, Oct. 14, 2016).*
RGD (https://www.ncbi.nlm.nih.gov/protein/?term=rgd, downloaded, Oct. 14, 2016).*
Kobayashi et al. (Jun Hirabayashi (ed.), Lectins: Methods and Protocols, Methods in Molecular Biology, vol. 1200, Chapter 45, DOI 10.1007/978-1-4939-1292-6_45, © Springer Science+Business Media New York 2014).*
Skolnick et al. (TIBTECH 18:34-39, 2000).*
Marincola et al. (Trends in Immunology, Jun. 2003, 334-341).*
Gura (Science, 1997, 278:1041-1042).*

(Continued)

*Primary Examiner* — Peter J Reddig
(74) *Attorney, Agent, or Firm* — McDonnell Boehnen Hulbert & Berghoff LLP

(57) ABSTRACT

The present invention relates to the treatment and prevention of cancer. The present invention relates to vaccines comprising solubilized components of cancer cells or cancer-associated cells. Moreover, the present invention also relates to methods of producing vaccines from biological samples comprising cancer cells or cancer-associated cells and using said vaccines for the treatment or prevention of cancer in subjects. The present invention also relates to methods of producing vaccines, in particular, autologous vaccines. The present invention also relates to therapeutic uses of mesenchymal stem cells and to methods of treatment and or prevention that comprise administering mesenchymal stem cells to a subject. The present invention also relates to methods of enhancing the efficacy of vaccines and methods for the treatment and prevention of cancer, and to compositions and kits suitable for use in the methods.

23 Claims, 17 Drawing Sheets

(56) References Cited

OTHER PUBLICATIONS

Kaiser (Science 2006, 31: 1370).*
Rudikoff et al. (PNAS USA, 1982, 79: 1979-1983).*
Coleman et al. (Research in Immunology, 1994; 145(1): 33-36).*
Ibragimova and Wade (Biophysical Journal, Oct. 1999, vol. 77, pp. 2191-2198).*
Zhang (Int. J. Cancer 2009 125: 124-132), (Year: 2009).*
Sulfo-NHS LC-Biotin (Sulfo NHS-X-Biotin) (www.covachem.com/sulfo_nhs_lc_biotin_127062-22-0.html, downloaded Oct. 6, 2017) (Year: 2017).*
Burgess RR (Methods in Enzymology 2009 463: 331-342) (Year: 2009).*
Turtoi et al. (J. Proteome Res. May 3, 2011 10: 3160-3182) (Year: 2011).*
Hughes, LE et al (1970) Cancer26: 269-278.
Billiau, A & Matthys, P (2001) Journal of Leukocyte Biology 70: 849-860.
Root-Bernstein, RS & Westall, FC (1990) Brain Res Bull. 25: 827-841.
Giannios J., "Gene modified cellular vaccine (GMCV) composed of autologous adipose-derived mesenchymal stem cells (AAD-MSCS) transfected with lipid-cation HSP70 activated innate and adaptive immunity after targeting metastatic pancreatic Ca cells", Gut, Apr. 2011, vol. 60, Supplement 1, p. A21, Abstract OC-042.
Seo S.H. et al., "The effects of mesenchymal stem cells injected via different routes on modified IL-12-mediated antitumor activity", Gene Therapy, May 2011, vol. 18, No. 5, pp. 488-495.
Kucerova L. et al. "Cytosine deaminase expressing human mesenchymal stem cells mediated tumour regression in melanoma bearing mice", The Journal of Gene Medicine, 2008, vol. 10, No. 10, pp. 1071-1082.
Root-Bernstein R.S. et al., "Serotonin binding sites. II. Muramyl dipeptide binds to serotonin binding sites on myelin basic protein, LHRH, and MSH-ACTH 4-10.", Brain Research Bulletin, Dec. 1990, vol. 25, No. 6, pp. 827-841.
Sigma Life Science, "Detergents and Solubilization Reagents", BioFiles for Life Science Research, 2008, vol. 3, No. 3, pp. 1-36. Retrieved from the Internet <URL:http://www.sigmaaldrich.com/content/dam/sigmaaldrich/docs/Sigma/General_Information/2/biofiles_issue3_3.pdf>.
Hsueh E.C., "Tumour Cell-Based Vaccines for the Treatment of Melanoma", BioDrugs, 2001, vol. 15, No. 11, pp. 713-720.
Hughes L.E. et al., "A study in clinical cancer immunotherapy", Cancer, 1970, vol. 26, pp. 269-278.
Laurean. McCann et al: Identification of Vascular Surface Proteins by in Vivo Biotinylation: A Method Sufficiently Sensitive to Detect Changes in Rat Liver 2 Weeks after Partial Hepatectomy. Journaolf Proteome Research, vol. 6, No. 8, Aug. 1, 2007 (Aug. 1, 2007), pp. 3188-311.
J F Hare et al: "Solubility in non-ionic detergents distinguishes between slowly and rapidly degraded plasma membrane proteins". Journal of Biological Chemistry, Feb. 25, 1994 (Feb. 25, 1994), p. 5981.
McCann, Laurean et al: "A proteomic strategy for identifying vascular surface proteins as potential targets for cancer treatment", American Association for Cancer Research. Proceedins of the Annual Meeting, American Associatio for Cancer Research, US, vol. 47, Apr. 15, 2006 (Apr. 15, 2006), p. 225.
Gao et al., "GM-CSF-surface modified B16.F10 melanoma cell vaccine", Vaccine, 24(25):5265-5268 (Jun. 2006).

* cited by examiner

A

B

VACCINES FOR THE TREATMENT OF CANCER AND COMPOSITIONS FOR ENHANCING VACCINE EFFICACY

TECHNICAL FIELD

The present invention relates to the treatment and prevention of cancer. The present invention relates to vaccines comprising solubilized components of cancer cells or cancer-associated cells. Moreover, the present invention also relates to methods of producing vaccines from biological samples comprising cancer cells or cancer-associated cells and using said vaccines for the treatment or prevention of cancer in subjects. The present invention also relates to methods of producing vaccines, in particular, autologous vaccines.

The present invention also relates to therapeutic uses of mesenchymal stem cells and to methods of treatment and or prevention that comprise administering mesenchymal stem cells to a subject. The present invention also relates to methods of enhancing the efficacy of vaccines and methods for the treatment and prevention of cancer, and to compositions and kits suitable for use in the methods.

CROSS-REFERENCE TO RELATED APPLICATIONS

This application claims the benefit of Australian Provisional Patent Application No. 2012905667 filed 24 Dec. 2012 entitled "Vaccines for treatment of cancer", and of Australian Provisional Patent Application No. 2012905669 filed 24 Dec. 2012 entitled "Vaccine booster", and of Australian Patent Application No. 2013203806 filed 11 Apr. 2013 entitled "Vaccines for the treatment or prevention cancer", and of Australian Provisional Patent Application No. 2013903592 filed 18 Sep. 2013 entitled "Vaccines for the treatment or prevention of cancer", and International Application No. PCT/AU2013/001523, filed 24 Dec. 2013 entitled "Vaccines for the treatment of cancer and compositions for enhancing vaccine efficacy", the contents of each of which are incorporated herein by reference in their entirety.

BACKGROUND OF THE INVENTION

Most cancer cells elicit an immune response that is evident by the presence of immune cell infiltrates and inflammation. This response, however, is not strong enough to overcome the cancer cell's defence strategies. Approaches taken to promote an immune response against cancer cells include stimulating a subject's immune cells, in particular, their dendritic cells, to recognise cancer-cell specific antigens in vitro and then injecting these back into the subject.

The molecular and cellular interaction between the immune system and a tumour is complex and it is only relatively recent that the importance of normal cells, tissues and chemokine/cytokine responses in this interaction has been recognised. Blood vessels, connective tissue, stroma and extra-cellular matrix all play a part in supporting tumour growth and the inflammatory environment supplied by the immune system further stimulates growth.

The lack of understanding of the complex interactions between tumours and the immune system has hindered the development of cancer immunotherapy. Approaches involving using purified tumour antigens and more complex mixtures of tumour antigens have failed to stimulate adequate immune responses against tumours. The reasons for this are unknown, but may include the genetic instability of tumours and the ability of tumours to evade the immune system by presenting a "normal" appearance or releasing inhibitors. Tumours can respond to an immune response by reducing the amount of targeted antigens, by masking antigens from the immune system or by expressing mutated versions of antigens that are no longer recognised. Such defensive strategies undermine the immune system, making it difficult to maintain an effective immune response at the level required to halt tumour growth and cause regression.

Mesenchymal stem cells (MSCs) are post-natal, multipotent, adult stem cells. Mesenchymal stem cells (MSCs) are present in many tissues in the body and play an important role in tissue repair and regeneration. For therapeutic purposes MSCs are commonly harvested from bone marrow, cord blood and adipose tissue. In many circumstances the cells are expanded by tissue culture prior to use. Adipose tissue has the unique advantage as a source of MSCs that such large numbers of MSCs are present in the tissue that for many applications the cells do not need to be expanded by tissue culture.

MSCs are currently being investigated as therapeutic agents for the treatment of various diseases including osteoarthritis, MS, rheumatoid arthritis, renal disease and heart disease.

SUMMARY OF THE INVENTION

There would be substantial benefit to being able to direct a cancer subject's immune system to assist in the treatment or prevention of cancer.

The inventors have surprisingly found that vaccines based on the solubilized components of cancer cells and normal cells associated with cancer cells, in combination with a non-mammalian polypeptide capable of binding a mammalian protein, are efficient at eliciting an immune response against a cancer cell.

Accordingly, in a first aspect of the present invention, there is provided a method for producing a vaccine for the treatment or prevention of cancer, the vaccine comprising solubilized components of a cancer cell or cancer-associated cell, and a non-mammalian polypeptide capable of binding a mammalian protein, the method comprising exposing a biological sample comprising at least one cancer cell or cancer-associated cell to an ionic detergent, a reducing agent, and a non-mammalian polypeptide capable of binding a mammalian protein, to produce a solubilized biological sample comprising components from said cancer cell or cancer-associated cell, and a non-mammalian polypeptide capable of binding a mammalian protein.

In particular embodiments of the present invention, the biological sample is a biological sample from the subject intended to receive the vaccine. In an embodiment the biological sample is a biological sample from a different individual of the same species as the subject intended to receive the vaccine.

In one embodiment of the first aspect, the ionic detergent is selected from the group consisting of sodium-dodecyl-sulphate (SDS), 3-[(3-Cholamidopropyl)dimethylammonio]-1-propanesulfonate (CHAPS), lithium dodecylsulphate, sodium cholate, sodium lauroylsarcosine and cetyltrimethylammonium bromide (CTAB). In another embodiment the biological sample is exposed to an ionic detergent at a concentration of 0.1 to 10% (w/v). In a preferred embodiment, the ionic detergent is SDS. In a further preferred embodiment, the biological sample is exposed to SDS at a concentration of 0.5 to 1.5% (w/v).

In another embodiment of the first aspect, the reducing agent is selected from the group consisting of 2-mercaptoethanol, 2-mercaptoethanolamine, cysteine-HCl, dithiothreitol (DTT), tris(2-carboxyethyl)phosphine (TCEP), tributylphosphine (TBP) and iodoacetamide. In a further embodiment, the biological sample is exposed to a reducing agent at a concentration of 1 mM to 500 mM. In a preferred embodiment, the reducing agent is TCEP or DTT. In a more preferred embodiment, the biological sample is exposed to TCEP or DTT at a concentration of 1 mM to 100 mM.

In a particular embodiment of the first aspect, the biological sample is exposed to an ionic detergent prior to exposure to a reducing agent and a non-mammalian polypeptide capable of binding a mammalian protein.

In other embodiments, the biological sample is exposed to an ionic detergent and a reducing agent prior to exposure to a non-mammalian polypeptide capable of binding a mammalian protein.

In one embodiment of the first aspect, the non-mammalian polypeptide capable of binding a mammalian protein is a bacterial lectin or adhesin. In another embodiment, the non-mammalian polypeptide capable of binding, a mammalian protein is a polypeptide with an RGD or RGD-like motif. In a preferred embodiment, the non-mammalian polypeptide is streptavidin, avidin or Neutravidin. In a particular preferred embodiment the non-mammalian polypeptide is streptavidin.

In a particular embodiment of the first aspect, the method further comprises exposing said solubilized biological sample to biotin. In a preferred embodiment the step of exposing the sample to biotin is performed before the sample is exposed to a non-mammalian polypeptide capable of binding a mammalian protein.

In another embodiment, the method further comprises exposing the biological sample to an alkylating reagent.

In one embodiment of the first aspect, the solubilized biological sample is partitioned into a soluble fraction and an insoluble fraction.

In particular embodiments of the first aspect, the method further comprises solvent precipitation of said solubilized biological sample or a soluble fraction of the solubilized biological sample, followed by resuspension of the resulting precipitate in a suitable liquid. In one embodiment, the solvent is a polar organic solvent. In a preferred embodiment, the polar organic solvent is selected from the group consisting of ethanol, methanol, acetone, isopropanol, propanol and DMF. In a further preferred embodiment, the polar organic solvent is acetone.

In a second aspect of the present invention, there is provided a method for producing a vaccine for the treatment or prevention of cancer, the method comprising the steps of:
  exposing a biological sample comprising at least one cancer cell or cancer-associated cell to an ionic detergent in a suitable liquid to produce a solubilized biological sample comprising soluble material and insoluble material;
  partitioning the soluble and insoluble material of the solubilized biological sample to produce a soluble fraction and an insoluble fraction;
  exposing the soluble fraction to a reducing agent;
  exposing the soluble fraction to a non-mammalian polypeptide capable of binding a mammalian protein;
  performing a solvent precipitation of the soluble fraction; and
  resuspending the precipitate in a suitable liquid.

In a third aspect of the present invention, there is provided a method for producing a vaccine for the treatment or prevention of cancer, the method comprising the steps of:
  a. exposing a biological sample comprising at one least cancer cell or cancer-associated cell to an ionic detergent and a reducing agent in a suitable liquid to produce a solubilized biological sample comprising soluble material and insoluble material;
  b. partitioning the soluble and insoluble material of the solubilized biological sample to produce a soluble fraction and an insoluble fraction;
  c. exposing the soluble fraction to a non-mammalian polypeptide capable of binding a mammalian protein;
  d. performing a solvent precipitation of the soluble fraction; and
  e. resuspending the precipitate in a suitable liquid.

In particular embodiments of the second and third aspects, the non-mammalian polypeptide capable of binding a mammalian protein is a bacterial lectin or adhesin. In other embodiments, the non-mammalian polypeptide capable of binding a mammalian protein is a polypeptide with an RGD or RGD-like motif. In preferred embodiments of the second and third aspects, the non-mammalian polypeptide is streptavidin, avidin or Neutravidin. In a particular preferred embodiment the non-mammalian polypeptide is streptavidin.

In further embodiments, the method further comprises the step of exposing said soluble fraction to biotin prior to performing said solvent precipitation of the soluble fraction. In a preferred embodiment the method further comprises exposing the soluble fraction to biotin before exposure to a non-mammalian polypeptide capable of binding a mammalian protein. In a preferred embodiment the method further comprises exposing the soluble fraction to biotin before exposure to a reducing agent.

In other embodiments, the method further comprises the step of exposing said soluble fraction to an alkylating reagent prior to performing said solvent precipitation of the soluble fraction.

The present invention also provides vaccines made by any of the methods herein described.

In a fourth aspect of the present invention, there is provided a vaccine for the treatment or prevention of cancer in a subject, wherein the vaccine comprises solubilized and reduced components of a cancer cell or cancer-associated cell, and a non-mammalian polypeptide capable of binding a mammalian protein.

In a fifth aspect of the present invention, there is provided a vaccine for the treatment or prevention of cancer in a subject, wherein the vaccine comprises solubilized, reduced and alkylated components of a cancer cell or cancer-associated cell, and a non-mammalian polypeptide capable of binding a mammalian protein.

In particular embodiments of the fourth and fifth aspects of the present invention, the cancer cell or cancer-associated cell is a cancer cell or cancer-associated cell from said subject.

In other embodiments, the non-mammalian polypeptide capable of binding a mammalian protein is a bacterial lectin or adhesin. In further embodiments, the non-mammalian polypeptide capable of binding a mammalian protein is a polypeptide with an RGD or RGD-like motif. In preferred embodiments, the non-mammalian polypeptide is streptavidin, avidin or Neutravidin. In a particular preferred embodiment the non-mammalian polypeptide is streptavidin.

In particular embodiments of the fourth and fifth aspects, the vaccine further comprises biotin. In a preferred embodiment the vaccine comprises biotin and streptavidin, with the biological sample or fraction thereof having been exposed to biotin before exposure to streptavidin.

In preferred embodiments, the method of the present invention is performed by a medical practitioner or by a person or persons under the supervision of a medical practitioner, or by a combination thereof.

In a sixth aspect of the present invention, there is provided a pharmaceutical composition for the treatment or prevention of cancer comprising any of the vaccines described herein, and a pharmaceutically acceptable carrier.

In a preferred embodiment, the pharmaceutical composition is used for the treatment or prevention of cancer in a subject.

In a seventh aspect of the present invention, there is provided a method of treatment or prevention of cancer in a subject, the method comprising administering an effective amount of a vaccine of the present invention to a subject.

In an eighth aspect of the present invention, there is provided the use of a composition comprising a solubilized biological sample of at least one cancer cell or cancer-associated cell, and a non-mammalian polypeptide capable of binding a mammalian protein, for the manufacture of a medicament for the treatment or prevention of cancer in a subject.

In particular embodiments of the present invention, the biological sample is a biopsy sample from a subject intended to be the recipient of the vaccine, medicament or treatment.

In a ninth aspect of the present invention, there is provided a method for the treatment or prevention of cancer in a human subject, the method comprising the steps of obtaining a biological sample comprising at least one cancer cell or cancer-associated cell from said subject, exposing the biological sample to an ionic detergent, a reducing agent, and a non-mammalian polypeptide capable of binding a mammalian protein, to produce a vaccine comprising a solubilized biological sample comprising components from said cancer cell or cancer-associated cell, and a non-mammalian polypeptide capable of binding a mammalian protein, and administering a therapeutically effective amount of said vaccine to said subject, wherein all steps of the method are performed by or under the supervision of a registered medical practitioner having prime responsibility for the clinical care of said subject throughout said method.

In particular embodiments of the ninth aspect, the method for treatment or prevention is a course of treatment or prevention comprising multiple steps of administering said vaccine to said patient. In an embodiment of the treatment methods of the invention, the vaccine is administered to a patient two times, or three times, or four times, or five times, or six times, or seven times, or more. In an embodiment a subsequent dose is administered to the patient about one to about four weeks after the previous dose.

In a further embodiment, one or more step(s) of the method is conducted by a person or persons under the supervision of said medical practitioner. In one embodiment, the collective steps of the method are performed by a plurality of individuals. In an embodiment, the collective steps of the method are performed at multiple locations. In one embodiment, the step of obtaining a biological sample from said subject is conducted at a different location to said exposing step.

In other embodiments, the method for the treatment or prevention of cancer in a human subject further comprises additional steps described herein for the production of said vaccine.

As described herein it has also surprisingly been found that MSCs can be used to enhance the therapeutic efficacy of a vaccine. The inventors have also surprisingly found the MSCs can be used to inhibit the progression of cancer cells.

In a tenth aspect of the invention there is provided a method of treating or preventing a disease or disorder in a subject, the method comprising administering to said subject a therapeutically effective amount of a vaccine specific for said disease or disorder, and a composition comprising mesenchymal stem cells.

In an embodiment the MCSs originate from adipose tissue or bone marrow. In an embodiment the MSCs originate from the subject intended to receive the vaccine and the composition. In a preferred embodiment the MSCs originate from a different individual of the same species as the subject intended to receive the vaccine and the composition. In a further preferred embodiment the MSCs originate from a different species to the subject intended to receive the vaccine. In an embodiment the MSCs are xenogeneic to the recipient subject.

In an embodiment the vaccine is a veterinary vaccine. In an embodiment the vaccine is a vaccine for use in treating or preventing a disease of canines, felines, bovines, porcines, ovines, or equines. In an embodiment the vaccine is a vaccine for use in treating or preventing a disease of humans.

In a preferred embodiment the vaccine is an anti-cancer vaccine. In an embodiment the anti-cancer vaccine is produced by a method described herein. In an embodiment the anti-cancer vaccine comprises solubilized and reduced components of cancer cells or cancer-associated cells. In an embodiment the anti-cancer vaccine comprising solubilized and reduced components of cancer cells or cancer-associated cells, further comprises a non-mammalian polypeptide capable of binding a mammalian protein. In an embodiment the anti-cancer vaccine comprises solubilized, reduced and alkylated components of cancer cells or cancer-associated cells, and a non-mammalian polypeptide capable of binding a mammalian protein. In an embodiment the cancer cells or cancer-associated cells are from the subject intended to receive the vaccine and the composition. In an embodiment administration is at or near the site of the tumour. In an embodiment administration is remote from the site of the tumor.

In an embodiment the MSCs originate from the subject intended to receive the composition and the anti-cancer vaccine is prepared from cancer cells or cancer-associated cells which originate from the subject intended to receive the composition.

In an embodiment the vaccine and the composition are administered to the subject at the same time. In an embodiment one or more of the vaccine and the composition comprising MSCs is or are administered to the subject multiple times. In an embodiment administration to the subject of the vaccine and the composition comprising MSCs is at or near the same site.

In an eleventh aspect of the invention there is provided a composition comprising MSCs, when used to enhance the therapeutic efficacy of a vaccine.

In a twelfth aspect of the invention there is provided a composition comprising MSCs, when used for the treatment or prevention of cancer in a subject.

In a thirteenth aspect of the invention there is provided a composition comprising MSCs, when used to enhance the therapeutic efficacy of an anti-cancer vaccine.

In a fourteenth aspect of the invention there is provided a composition comprising a vaccine and MSCs.

In an embodiment the vaccine is a veterinary vaccine. In an embodiment the vaccine is a vaccine for use in treating or preventing a disease of canines, felines, bovines, porcines, ovines, or equines. In an embodiment the vaccine is a vaccine for use in treating or preventing a disease of humans.

In an embodiment the vaccine is an anti-cancer vaccine.

In an embodiment the anti-cancer vaccine is produced by a method described herein. In an embodiment the anti-cancer vaccine comprises solubilized and reduced components of cancer cells or cancer-associated cells. In an embodiment the anti-cancer vaccine comprises solubilized and reduced components of cancer cells or cancer-associated cells, and a non-mammalian polypeptide capable of binding a mammalian protein. In an embodiment the anti-cancer vaccine comprises solubilized, reduced and alkylated components of cancer cells or cancer-associated cells, and a non-mammalian polypeptide capable of binding a mammalian protein. In an embodiment the non-mammalian polypeptide is streptavidin, avidin or Neutravidin. In a particular preferred embodiment the non-mammalian polypeptide is streptavidin. In an embodiment the cancer cells or cancer-associated cells are from the subject intended to receive the composition.

In an embodiment the MCSs originate from adipose tissue or bone marrow. In an embodiment the MSCs originate from the subject intended to receive the composition. In an embodiment the anti-cancer vaccine is prepared from cancer cells or cancer-associated cells which originate from the subject intended to receive the composition. In an embodiment the MSCs originate from the subject intended to receive the composition and the anti-cancer vaccine is prepared from cancer cells or cancer-associated cells which originate from the subject intended to receive the composition. In a preferred embodiment the MSCs originate from a different individual of the same species as the subject intended to receive the composition. In an embodiment the MSCs are allogeneic to the recipient subject. In a further preferred embodiment the MSCs originate from a different species to the subject intended to receive the vaccine. In an embodiment the MSCs are xenogeneic to the recipient subject.

In a fifteenth aspect of the invention there is provided a method for the treatment or prevention of cancer in a subject, the method comprising administering to said subject a composition comprising MSCs. In an embodiment the method further comprises administering to said subject an anti-cancer vaccine. In an embodiment the anti-cancer vaccine is produced by a method described herein.

In an embodiment the anti-cancer vaccine comprises solubilized and reduced components of cancer cells or cancer-associated cells. In an embodiment the anti-cancer vaccine comprising solubilized and reduced components of cancer cells or cancer-associated cells, further comprises a non-mammalian polypeptide capable of binding a mammalian protein. In an embodiment the anti-cancer vaccine comprises solubilized, reduced and alkylated components of cancer cells or cancer-associated cells, and a non-mammalian polypeptide capable of binding a mammalian protein. In an embodiment the cancer cells or cancer-associated cells are from the subject intended to receive the composition. In an embodiment the MSCs originate from the subject intended to receive the composition. In an embodiment the MSCs originate from the subject intended to receive the composition and the anti-cancer vaccine is prepared from cancer cells or cancer-associated cells which originate from the subject intended to receive the composition. In an embodiment the MCSs originate from adipose tissue or bone marrow.

In an embodiment the vaccine and the composition are administered to the subject at the same time. In an embodiment the MSCs are allogeneic to the recipient subject. In an embodiment the MSCs are xenogeneic to the recipient subject.

In a sixteenth aspect of the invention there is provided a method for the treatment or prevention of cancer in a human subject, the method comprising the steps of:

obtaining a biological sample comprising at least one cancer cell or cancer-associated cell from said subject, exposing the biological sample to an ionic detergent, a reducing agent, and a non-mammalian polypeptide capable of binding a mammalian protein, to produce an anti-cancer vaccine comprising a solubilized biological sample comprising components from said cancer cell or cancer-associated cell, and a non-mammalian polypeptide capable of binding a mammalian protein, and administering a therapeutically effective amount of said vaccine to said subject; and obtaining a biological sample comprising MSCs from said subject, isolating MSCs from the biological sample and preparing a composition comprising MSCs, and administering a therapeutically effective amount of said composition comprising MSCs to said subject;

wherein all steps of the method are performed by or under the supervision of a registered medical practitioner having prime responsibility for the clinical care of said subject throughout said method.

In a seventeenth aspect of the invention there is provided a method for enhancing the efficacy of a vaccine in a human subject, the method comprising the steps of:

administering a therapeutically effective amount of a vaccine to said subject; and obtaining a biological sample comprising MSCs from said subject, isolating MSCs from the biological sample and preparing a composition comprising MSCs, and administering a therapeutically effective amount of said composition comprising MSCs to said subject;

wherein all steps of the method are performed by or under the supervision of a registered medical practitioner having prime responsibility for the clinical care of said subject throughout said method.

It will be understood that the embodiments relate to all aspects of the invention as appropriate.

DEFINITIONS

Throughout this specification, reference to "a" or "one" element does not exclude the plural, unless context determines otherwise.

The term "treatment", and the like, in the context of the present specification and with particular reference to treatment of cancer includes any of the alleviation of the symptoms associated with a cancer, as well as cancer regression and remission. In certain embodiments a treatment will slow, delay or halt the proliferation or metastasis of a cancer, prevent differentiation of a cell line, or reverse the progression of one or more tumours, at least temporarily. The treatment may cure the cancer, or delay morbidity. Hence, in the context of this invention the word "treatment" or derivations thereof when used in relation to a therapeutic application relevant to cancer includes all aspects of a therapy, such as the alleviation of pain associated with the cancer being treated, alleviation of the severity of the cancer being treated, improvement in one or more symptoms of the cancer being treated, improvement in the overall well-being of the subject being treated. Use of the word "treatment" or derivatives thereof will be understood to mean that the subject being "treated" may experience any one or more of the aforementioned benefits.

The term "prevention", and the like, in the context of the present specification and with particular reference to prevention of cancer refers to the prevention of the recurrence of all or some of the symptoms associated with a cancer after a remission of said cancer, as well as the prevention of the formation of one or more cancers due to, for example, the metastasis of a cancer. The prevention may prevent morbidity due to one or more cancers, or delay morbidity due to one or more cancers.

The term "treatment", and the like, in the context of the present specification includes any of the alleviation of symptoms associated with a disease or disorder. By "disease" or "disorder" is meant any abnormal condition that affects the body of a subject, whereby the subject would benefit from medical intervention to treat or prevent the abnormal condition. In certain embodiments a treatment will slow, delay or halt the progress of a disease or disorder. The treatment may cure the disease or disorder, or delay morbidity. Hence, in the context of this invention the word "treatment" or derivations thereof when used in relation to a therapeutic application includes all aspects of a therapy, such as the alleviation of pain associated with the disease or disorder being treated, alleviation of the severity of the disease or disorder being treated, improvement in one or more symptoms of the disease or disorder being treated, improvement in the overall well-being of the subject being treated. Use, of the word "treatment" or derivatives thereof will be understood to mean that the subject being "treated" may experience any one or more of the aforementioned benefits a consequence of the therapeutic effect of the treatment.

The term "prevention", and the like, in the context of the present specification refers to the prevention of all or some of the symptoms associated with a disease or disorder, and/or the prevention of the recurrence of all or some of the symptoms associated with a disease or disorder. The prevention may prevent or delay morbidity due to a disease or disorder.

In the context of this specification, the term "comprising" means including, but not necessarily solely including. Furthermore, variations of the word "comprising", such as "comprise" and "comprises", have correspondingly varied meanings. Hence, the term "comprising" and variations thereof is used in an inclusive rather than exclusive meaning such that additional integers or features may optionally be present in a composition, method, etc. that is described as comprising integer A, or comprising integer A and B, etc.

In the context of this specification the term "about" will be understood as indicating the usual tolerances that a skilled addressee would associate with the given value.

In the context of this specification, where a range is stated for a parameter it will be understood that the parameter includes all values within the stated range, inclusive of the stated endpoints of the range, as well as including subranges which may be selected from within a stated broader range.

In the context of this specification, the term "plurality" means any number greater than one.

In the context of the specification, a "vaccine" is meant any substance used to stimulate the production of antibodies in a subject, whereby one or more components of the substance is/are recognised by the subject's immune system as immunogenic and/or antigenic. It is to be understood that the vaccines referred to herein, in the context of the use of mesenchymal stem cells, are not restricted to anti-cancer vaccines.

DETAILED DESCRIPTION

Anti-cancer Vaccines

Figure 1:
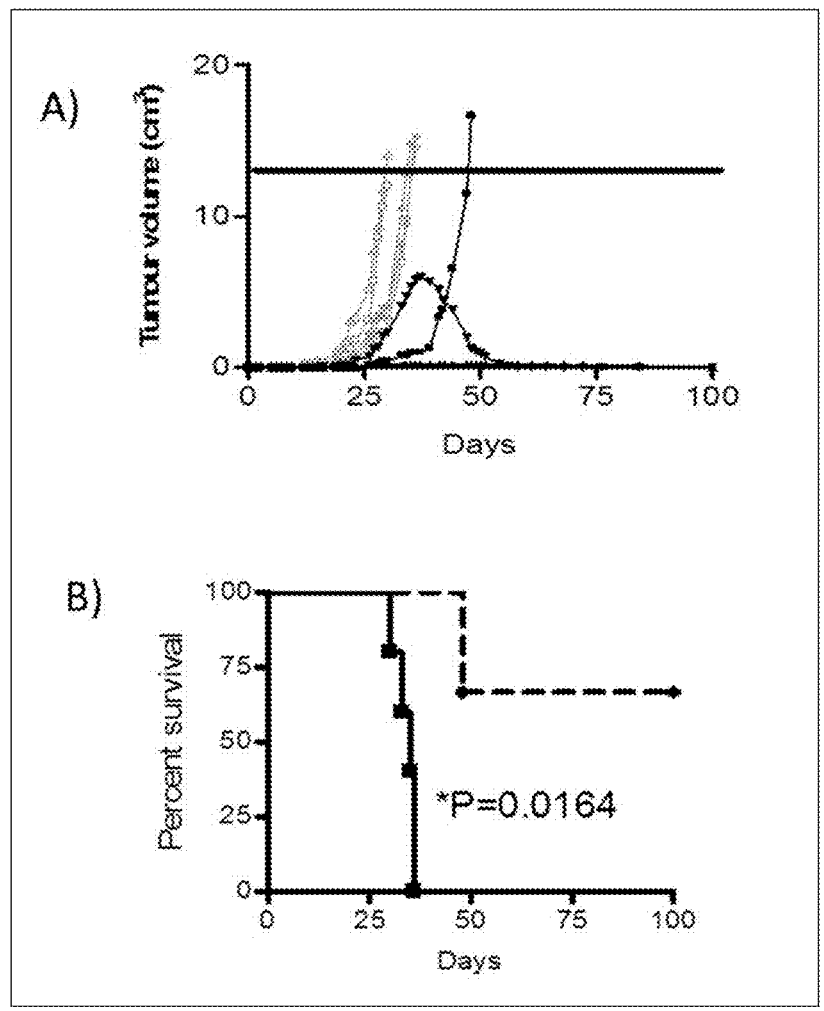
FIG. 1 shows the results from the initial vaccine trial. A) Tumour growth in control rats (adjuvant only, grey line, n=5) and rats pre-vaccinated (black line, n=3). Rats were challenged with approximately $1 \times 10^6$ 9L tumour cells in the flank at day zero. B) Survival curves for the same rats with solid line for controls (n=5) and dashed line for vaccine treated (n=3).

The inventors have surprisingly found that vaccines comprising heterologous mixtures of solubilized and reduced self and non-self proteins, polypeptides and cellular components, can generate an enhanced immune response to cancer cells in cancer patients. The invention may be used to produce these vaccines and pharmaceutical compositions for the treatment or prevention of cancer. Such vaccines are herein generally referred to as anti-cancer vaccines or as cancer vaccines, the terminology being used interchangeably. The cancer intended to be treated, or prevented, may be any cancer, such as those mentioned herein.

Accordingly, the present invention provides a method for producing a vaccine for the treatment or prevention of cancer, the vaccine comprising solubilized components of a cancer cell or a cancer associated cell, and a non-mammalian polypeptide capable of binding a mammalian protein, the method comprising exposing a biological sample comprising at least one cancer cell or cancer-associated cell to an ionic detergent, a reducing agent, and a non-mammalian polypeptide capable of binding a mammalian protein, to produce a solubilized biological sample comprising components from said cancer cell or cancer-associated cell, and a non-mammalian polypeptide capable of binding a mammalian protein.

A vaccine may be any substance used to stimulate the production of antibodies against one or several cancers, whereby the substance is recognised by the subject's immune system as immunogenic and/or antigenic.

The cancer cell may be from any cancer that presents as a solid tumour or a blood (liquid) cancer, including, but not limited to sarcomas, carcinomas, lymphomas, leukemias, myelomas and circulating tumour cells (CTCs). For example, the carcinoma may be that of the bladder, breast, brain, colon, mesothelioma, kidney, liver, lung, including small cell lung cancer, non-small cell lung cancer, head and neck, oesophagus, gall bladder, ovary, pancreas, stomach, cervix, thyroid, prostate or skin.

As further non-limiting examples, the lymphoma may be B-cell lymphoma, T-cell lymphoma, Hodgkins lymphoma, non-Hodgkins lymphoma, hairy cell lymphoma, mantle cell lymphoma, myeloma, Burkett's lymphoma, or an extranodal lymphoma of the stomach, breast or brain.

The sarcoma may, for example, be fibrosarcoma, rhabdomyosarcoma, chondrosarcoma, leiomyosarcoma, mesothelial sarcoma, angiosarcoma, liposarcoma, tumours of the central and peripheral nervous system, including astrocytoma, neuroblastoma, glioma and schwannomas, or other tumours, including melanoma, seminoma, teratocarcinoma, osteosarcoma, xenoderoma pigmentosum, keratoctanthoma, thyroid follicular cancer and Kaposi's sarcoma.

The myeloma may, for example, be plasma cell myeloma or Kahler's disease or multiple myeloma. In other examples, the leukemia may be myelogenous leukemia, granulocytic leukemia, lymphatic leukemia, lymphocytic leukemia or lymphoblastic leukemia, polycythemia vera or erythremia.

The biological sample may be any sample from a subject which includes at least one cancer cell or cancer-associated cell, including, but not limited to tissue, tissue fluids, blood, blood components, bone marrow, excreta including urine and feces, and secreta including mucus. The biological sample may be more than one type. For example, a biological sample may be comprised of a tissue sample and a blood sample. The biological sample may comprise a tissue sample from one site on a subject and a tissue sample from another site on a subject. The biological sample may comprise more than one sample taken from a subject at different times. For example, a biological sample may comprise two blood samples that are taken from a subject on two separate occasions.

In a preferred embodiment, the biological sample comprises a biopsy of a known or suspected cancer or tumour. The biological sample comprising at least one cancer cell or cancer-associated cell may, for example, be a tumour sample. The biological sample will typically comprise cancer cells and non-cancer cells, and non-cellular components such as, for example, plasma, extra-cellular matrix, enzymes, growth factors and cytokines.

The biological sample may be collected from a subject under the clinical care of a medical practitioner by, for example, a medical practitioner or a health care professional. A medical practitioner may be any person that is registered, authorized or certified under law to practice medicine independently. A health care professional may be any person that is permitted, authorized, registered or certified to collect a biological sample from a subject either independently or under the supervision of a medical practitioner. For example, the health care professional may be a registered or enrolled nurse, or a medical practitioner's assistant or a clinical assistant. It would be understood that the biological sample may, for example, be collected during routine out-patient procedures that would ordinarily be carried out on a subject with cancer who is under the clinical care of a medical practitioner.

In a particular embodiment, the method of the present invention is performed by a medical practitioner or by a person or persons under the supervision of a medical practitioner, or by a combination thereof. A person under the supervision of a medical practitioner may be, for example, a health care professional, a pharmacist, a clinical, medical or pathology laboratory technician, or a scientist. It would be understood that the method of the present invention may be performed in any laboratory by a medical practitioner or by a person or persons under the supervision of a medical practitioner, or by a combination thereof.

The biological sample may contain at least one cancer cell from a cancer, such as any of the cancers mentioned herein. The cancer cell may be from one of more of these types of cancers. For example, a blood sample may contain cancer cells that are B-cell lymphoma cells as well as cancer cells that are melanoma cells. Furthermore, a tissue sample may contain cancer cells that are fibrosarcoma cells as well as cancer cells that are liposarcoma cells.

The vaccines of the present invention may prevent or delay or retard the development of cancers that, for example, may ordinarily develop from the metastasis of any of the cancers mentioned herein. The vaccines of the present invention may also prevent or delay or retard the recurrence of any of the cancers mentioned herein after treatment.

The cancer-associated cell may be any non-cancer cell included in the biological sample due to proximity to a cancer cell. The cancer-associated cell may be from any proximal non-cancerous tissue, including, but not limited to blood vessels, connective tissue, nerves, muscle, brain tissue, stroma, tissue from associated organs and fatty tissues. The cancer-associated cell may be any non-cancer cell, including, but not limited to a white blood cell, a red blood cell, a plasma cell, a fibroblast, or a stem cell.

In one embodiment of the present invention, the biological sample is from the subject that is the intended recipient of the vaccine produced using said biological sample. In this context, the vaccine may be referred to as autologous.

The solubilization of a biological sample is understood to mean the disruption of a biological sample in a liquid phase by any appropriate means, typically by chemical, mechanical and/or physical means. The disruption of a biological sample includes, but is not limited to, the disintegration of tissue samples, dissociation of cells from tissues samples, disaggregation of cells, permeabilisation of cell membranes, cell lysis, dissolution of membranes and denaturation of proteins and polypeptides, and the disruption of inter- and intramolecular interactions, including but not limited to disulphide bonds, ionic bonds, hydrogen bonds, hydrophobic bonds and van der Waals.

Disruption of the biological sample, and hence solubilization, may be assisted by freeze/thaw cycles, agitation, vortexing, sheering, cutting, grinding, homogenizing, pressure forces, or sonic forces. For example, the solubilization of a biological sample by exposure to an ionic detergent and a reducing agent may be assisted by passing the material through a syringe and needle, grinding the material in a mortar and pestle, a homogenizer, a French press, a sonicator or a rotary device.

A person of skill in the art will understand that a solubilized biological sample will typically include soluble material and insoluble material. Insoluble material may be any material that will form a pellet when a solubilized biological sample is centrifuged at speeds over 1000 rpm (or equivalent) or above. The solubilized biological sample may comprise, for example, 10% to 99% (w/w) soluble material. For example, the solubilized biological sample may comprise approximately 20% (w/w) soluble material and approximately 80% (w/w) insoluble material, or the solubilized biological sample may comprise approximately 60% (w/w) soluble material and approximately 40% (w/w) insoluble material. In preferable circumstances, at least 50% (w/w) of the solubilized biological sample will be soluble material. It will also be understood by a skilled addressee that the amount of insoluble material and soluble material in the solubilized biological sample will depend on numerous factors including the type of biological sample, the amount of ionic detergent and reducing agent and the type of ionic detergent and reducing agent. For example, a solubilized biological sample derived from a tissue sample may comprise more insoluble material than a solubilized biological sample derived from a blood sample of the same volume. Furthermore, a biological sample that is exposed to a weak ionic detergent may produce a solubilized biological sample with more insoluble material than a solubilized biological sample produced by exposing a biological sample to a strong ionic detergent.

The biological sample may be solubilized in any suitable liquid. The liquid may be water or a solution, or salt solution or a buffered solution. The liquid may be a buffered salt solution, including, but not limited to, phosphate-buffered saline (PBS) or tris-buffered saline (TBS).

In the methods of the present invention, the biological sample is exposed to an ionic detergent. As used herein, an ionic detergent is understood to mean an amphipathic molecule, with a charged polar head group, which aids in solubilization of the components of tissues and cells. Ionic detergents include, but are not limited to, alkyl-aryl-sulphonates, long-chain alcohol-sulphates, olefine-sulphates and -sulphonates, alpha olefin-sulphates-sulphates and -sulphonates, sulphated monoglycerides, the sulphated ethers, the sulphosuccinates, the alkane-sulphonates, the phosphate-esters and the alkyl isethionates.

In one embodiment of the present invention, a biological sample is exposed to an ionic detergent selected from the group consisting of sodium-dodecyl-sulphate (SDS), 3-[(3-Cholamidopropyl)dimethylammonio]-1-propanesulfonate (CHAPS), lithium dodecylsulphate, sodium cholate, sodium lauroylsarcosine and cetyltrimethylammonium bromide (CTAB).

The biological sample may be exposed to an ionic detergent at any concentration appropriate to assist in achieving solubilization, such as concentrations between 0.1% (w/v) to 10% (w/v). For example, the concentration of the ionic detergent may be in the range of 0.1 to 1%, 0.5 to 2%, 1% to 5%, 2.5 to 7.5% or 5 to 10% (w/v). It will be understood to a person skilled in the art that the type of ionic detergent and final concentration of ionic detergent required to solubilize the biological sample will be influenced by multiple factors, including the amount of biological sample, the suitable liquid chosen, the solubility profile of the detergent, the type of biological sample and the use of adjunct agents or methods to assist solubilization. For example, solubilizing a biological sample that is a tissue sample comprising tumour tissue and tumour-associated connective tissue may require a higher concentration of ionic detergent than solubilizing a biological sample that is a tissue sample comprising tumour tissue with no tumour-associated connective tissue. Alternatively, solubilizing a small biological sample in a relatively large volume may require a lower concentration of ionic detergent than solubilizing a large biological sample in a relatively small volume. Furthermore, solubilizing a biological sample with a strong detergent, such as SDS, may require a lower concentration of ionic detergent than solubilizing a biological sample with a weaker detergent, such as sodium lauroylsarcosine.

In a preferred embodiment of the present invention, the biological sample is exposed to SDS at a concentration of 0.1% (w/v) to 10% (w/v). In a further preferred embodiment of the present invention, the concentration of the SDS is in the range of 0.5% (w/v) to 1.5% (w/v). For example, the concentration of the SDS may be in the range of 0.1 to 0.5%, 0.5 to 1%, 0.5 to 0.75%, 0.75% to 1.25, or 1% to 1.5% (w/v)

The method of the present invention comprises exposing the biological sample to a reducing agent. A reducing agent in the context of the present invention is understood to mean a compound that is capable of reducing disulphide bonds within and between proteins and polypeptides. The skilled addressee will understand that exposing the biological sample to a reducing agent will typically result in a biological sample comprising proteins and polypeptides with reduced disulphide bonds, as well as proteins and polypeptides with disulphide bonds that have not been reduced. The biological sample may, for example, be exposed to the reducing agent at the same time as the biological sample is exposed to the ionic detergent or after the biological sample is exposed to the ionic detergent.

In one embodiment of the present invention, the reducing agent is selected from the group consisting of 2-mercaptoethanol, 2-mercaptoethanolamine, cysteine-HCl, dithiothreitol (DTT), tris(2-carboxyethyl)phosphine (TCEP), tributylphosphine (TBP) and iodoacetamide. In one embodiment of the present invention, the reducing agent is TCEP. In another embodiment, the reducing agent is DTT.

In one embodiment, the biological sample is exposed to the reducing agent at a concentration ranging from 1 mM to 500 mM. For example, the concentration may be 1 mM to 10 mM, 5 mM to 20 mM, 10 mM to 50 mM, 25 mM to 100 mM, 75 mM to 250 mM, 200 mM to 300 mM or 250 mM to 500 mM. The skilled addressee will understand that the type of reducing agent and concentration of reducing agent used to solubilize the biological sample will typically depend on multiple factors including the type of biological sample, the amount of biological sample, the buffering strength and pH of the suitable liquid chosen, and the strength of the reducing agent. For example, solubilizing a biological sample with a strong reducing agent, such as TCEP, may require a lower concentration of reducing agent than solubilizing a biological sample with a weaker reducing agent, such as DTT. Furthermore, solubilizing a biological sample which is a tissue sample comprising a disulphide-rich connective tissue may require a higher concentration of reducing agent than solubilizing a biological sample which is a blood sample comprising red blood cells, that have less disulphide bonds.

In one embodiment, the biological sample is additionally exposed to an alkylating agent. Exposing a biological sample that comprises proteins and polypeptides, which have previously been exposed to a reducing agent, to an alkylating agent may modify some or all of the reduced cysteine residues in proteins and polypeptides by the addition of an alkyl group. This may maintain the oxidised state of some or all of the cysteine residues and may, for example, prevent the cysteine residues from forming or reforming a disulphide bond with other cysteine residues. Non-limiting examples of alkylating reagents that may be used in the methods of the present invention are iodoacetamide, acrylamide, 4-vinylpyridine, N-ethylmalemide and derivatives thereof. The skilled addressee will understand that the type of alkylating agent and concentration used will typically depend on the reducing agent used, as well as the same multiple factors considered when determining the type of reducing agent and concentration of reducing agent used. For example, a biological sample that has been exposed to the reducing agent may be exposed to an alkylating agent at a concentration that is a molar excess over the concentration of the reducing agent in the biological sample. In another example, a biological sample that has been exposed to the reducing agent TCEP at a concentration of 5 mM may then be exposed to iodoacetamide at a concentration of 10 m, whereas a biological sample that has been exposed to the reducing agent DTT at a concentration of 5 mM may then be exposed to iodoacetamide at the higher concentration of 15 mM, because DTT is known to react with alkylating agents.

In one embodiment of the present invention, the method further comprises exposing a solubilized biological sample to biotin. The skilled addressee will be aware of methods for biotinylation. In a preferred embodiment the biotinylation occurs before exposure to the non-mammalian polypeptide capable of binding a mammalian protein.

The biotin may be synthetic or extracted from an organism. It is believed that the biotin binds to the proteins, carbohydrates and lipids of the solubilized biological sample. Not wishing to be bound by theory, this may result in increased binding between the polypeptide with an RGD or RGD-like motif and the proteins, carbohydrates and lipids of the solubilized biological sample, because biotin binds to RGD and RGD-like motifs. This may assist in presenting the proteins, carbohydrates and lipids of the solubilized components of the cancer cells or cancer-associated cells to the immune system of the subject, which may enhance the immune response.

Additionally or alternatively, a reagent may be used that causes biotin to become covalently attached to the proteins, carbohydrates and/or lipids of the solubilized biological sample. A non-limiting example of a suitable reagent for this purpose is N-hydroxysuccinimidobiotin. The biotinylated proteins, carbohydrates and/or lipids may be bound to streptavidin through their biotin binding sites. The proteins, carbohydrates and/or lipids of the solubilized biological sample may thus have at least two ways of binding to streptavidin, through an RGD-like site and/or through the biotin-binding site on streptavidin. The methods of the present invention also comprise exposing the biological sample to a non-mammalian polypeptide capable of binding a mammalian protein.

The non-mammalian polypeptide can be any exogenous polypeptide, derived from a non-mammalian organism. A person of skill in the art will understand that, in this instance, an exogenous polypeptide is any polypeptide that is not present in the biological sample when it is taken from the subject. The non-mammalian organism may, for example, be a eukaryotic or prokaryotic, including but not limited to, birds, reptiles, fish, amphibians, bacteria, yeast, virus or fungus. In this context, it will be understood that "derived from a non-mammalian organism" does not require the polypeptide to be a naturally occurring polypeptide that has been extracted from the non-mammalian organism. The polypeptide may be synthetic, recombinant or extracted from an organism. The polypeptide may be a variant of a naturally occurring polypeptide, such as a fragment thereof, or a sequence variant, having the capability of binding a mammalian protein.

The polypeptide may be of any appropriate length, such as, for example, 10 to 1000 amino acids. For example, the polypeptide may comprise 10 to 100 amino acids, 50 to 500 amino acids, 25 to 150 amino acids, 250 to 750 amino acids, 500 to 100 amino acids, 400 to 800 amino acids, 500 to 750 amino acids, 750 to 900 amino acids, or 850 to 1000 amino acids.

Many non-mammalian organisms express polypeptides that are capable of binding mammalian proteins. Within the cell, these polypeptides may be utilized as, for example, receptors for cell-cell attachment, cell adhesion, docking and/or communication. A non-mammalian polypeptide may, for example, bind a mammalian protein non-specifically through intermolecular interactions, or specifically through mechanisms that rely on specific binding motifs and/or specific receptor-ligand interactions.

In particular, microbes display cell-surface polypeptides capable of binding mammalian proteins. Non-limiting examples of categories of these polypeptides are the lectins, the adhesins and the hemagglutinins. These polypeptides can act as receptors for attachment to ligands associated with mammalian cells. In one embodiment of the present invention, the non-mammalian polypeptide is a bacterial lectin or adhesin.

In one embodiment of the present invention, the non-mammalian polypeptide capable of binding a mammalian protein is a polypeptide with a tripeptide Arginine-Glycine-Aspartic acid (RGD) motif, or RGD-like motif. The RGD-like motif may be a tripeptide Arginine-Tyrosine-Aspartic acid (RYD) motif. As an illustrative example, the RGD and RGD-like motifs are found in many prokaryotic and eukaryotic adhesion-related proteins. In another embodiment of the present invention, the polypeptide with the RGD or RGD-like motif is streptavidin, avidin or Neutravidin. Streptavidin, avidin and Neutravidin have very similar properties, which each commonly known to, at least, bind biotin with high affinity. Neutravidin is a deglycosylated version of avidin, but may be used interchangeably with avidin or streptavidin. In preferred embodiments exemplified herein the non-mammalian polypeptide capable of binding a mammalian protein is streptavidin.

In one embodiment of the method of the present invention, the biological sample is exposed to an ionic detergent prior to exposing the biological sample to a reducing agent, and a non-mammalian polypeptide capable of binding a mammalian polypeptide.

In another embodiment of the method present invention, the biological sample is exposed to an ionic detergent and a reducing agent prior to exposing the biological sample to a non-mammalian polypeptide capable of binding a mammalian polypeptide.

In a further preferred embodiment, the method of the present invention further comprises a solvent precipitation of the solubilized biological sample. Solvent precipitation comprises adding an appropriate volume of a solvent to a sample. In a typical solvent precipitation, approximately 1 to 10 volumes of solvent is added to the sample. By "volume/s" is meant a volume equivalent to that of the sample that is the subject of the solvent precipitation. For example, if the sample is 500 µl, then 2 volumes would be 1000 µl. After adding the solvent, the final volume would be 1500 µl. The solvent precipitation step may comprise adding 1 to 2 volumes, 1 to 4 volumes, 2.5 volumes, 2 to 6 volumes, 5 volumes, 4 to 8 volumes, 7.5 volumes or 5 to 10 volumes.

In one embodiment of the present invention, the solvent is a polar organic solvent. In a further embodiment, the solvent is selected from the group consisting of ethanol, methanol, acetone, isopropanol, propanol and dimethylformamide (DMF). In a one embodiment, the solvent is acetone. The skilled addressee will understand that the type and volume of solvent to be added will typically be determined by multiple factors including the solvent properties, the concentration of the material to be precipitated and the liquid that the material is in, and the volatility of the solvent. Adding a solvent to a heterogeneous mixture of proteins, carbohydrates and lipids may result in some or all of these molecules forming insoluble aggregates due to the exposure of hydrophobic regions. This insoluble material may be harvested as a precipitate and the precipitate resuspended in any suitable liquid. The precipitate may be harvested by any appropriate method, such as by centrifugation, filtration or sedimentation. It is hypothesized that performing a solvent precipitation may enhance the immunogenicity of the resultant vaccine by making the proteins and carbohydrates appear even more foreign to the immune system. It also provides a simple means of concentrating the vaccine and removing the detergent and reducing agent from the vaccine prior to formulation into a medicament.

In one embodiment of the present invention, the method further comprises partitioning the solubilized biological sample into a soluble fraction and an insoluble fraction at any time prior to solvent precipitation. The insoluble fraction may be discarded. For example, if the solubilized biological sample is partitioned prior to exposure of the biological sample to a reducing agent, only the soluble fraction need be exposed to the reducing agent and the non-mammalian polypeptide capable of binding the mammalian protein.

The skilled addressee will understand that any appropriate method for partitioning the soluble and insoluble fractions may be used. For example, the soluble and insoluble fractions may be partitioned by centrifugation, filtration or sedimentation. The partitioned fractions may be separated by a physical barrier or may be present in the same container. For example, the solubilized biological sample may be centrifuged to produce a pellet comprising the insoluble fraction and a liquid phase comprising the soluble fraction, but the fractions may be present in the same container in which the solubilized biological sample was centrifuged in. The soluble fraction may be transferred to another container resulting in the fractions being separated by a physical barrier.

The method of the present invention results in a heterologous composition which typically may include denatured, partially denatured and non-denatured proteins, lipids, carbohydrates and nucleic acids, any or all of which may elicit immune responses. The heterologous mixture may contain proteins, lipids, carbohydrates and nucleic acids from cancer cells, as well from cancer-associated cells, such as, for example, non-cancer blood cells and cells from non-cancerous tissues. Not wishing to be bound by theory, it is hypothesized that the methods of the present invention result in a solubilized biological sample with modified proteins, lipids, carbohydrates and nucleic acids that appear foreign to the immune system and elicit an immune response.

The inventors believe that exposing the biological sample to a non-mammalian polypeptide capable of binding a mammalian protein during the method of the present invention aids in the efficacy of the vaccine because the polypeptide is exogenous, which will be recognized as foreign by the subject's immune system and stimulate the immune response. It is suggested here that this may facilitate the presentation of the components of the cancer cells or cancer-associated cells to the immune system, as well as assist in making the components appear more foreign to the immune system, which may enhance the immune response.

A particular embodiment of the present invention provides a method of producing a vaccine for the treatment or prevention of cancer comprising exposing a biological sample comprising at least one cancer cell or cancer-associated cell to an ionic detergent in a suitable liquid to produce a solubilized biological sample comprising soluble material and insoluble material, followed by partitioning the soluble and insoluble material of the solubilized biological sample to produce a soluble fraction and an insoluble fraction. The resulting soluble fraction is exposed to a reducing agent, and then exposed to a non-mammalian polypeptide capable of binding a mammalian protein. This mixture is solvent precipitated and the precipitate is resuspended in a suitable liquid. In one embodiment of this method, the non-mammalian polypeptide is streptavidin, avidin or Neutravidin. In an alternative embodiment, the partitioning of the solubilized biological fraction is performed after the biological sample is exposed to the ionic detergent and the reducing agent. In a further embodiment, the method also comprises the step of exposing the soluble fraction to biotin prior to solvent precipitation. In yet another embodiment, the method also comprises exposing the soluble fraction to an alkylating agent prior to solvent precipitation.

In embodiments of the present invention, the methods described herein permit the production of a therapeutic product of human origin which satisfies the requirements of for exclusion from regulation by the Australian Therapeutic Goods Administration (TGA) of goods manufactured and used in medical practice. The TGA is part of the Australian government Department of Health and Human Aging and is responsible for regulating medicines and medical devices. Under the relevant provisions, human cells and tissues or therapeutic goods manufactured therefrom, may be excluded from the requirement of inclusion in the Australian Register of Therapeutic Goods (ARTG) and from compliance with TGA legislation. The provision applies to human cells and tissues that are collected from a patient who is under the clinical care and treatment of a medical practitioner registered under a law of a State or an internal Territory; and manufactured by that medical practitioner, or by a person or persons under the professional supervision of that medical practitioner, for therapeutic application of a single indication and in a single course of treatment of that patient by the same medical practitioner, or by a person or persons under the professional supervision of the same medical practitioner. The relevant provision thus requires that the product is for autologous use only.

Consistent with those requirements, the present invention provides a method for the treatment or prevention of cancer in a human subject, the method comprising the steps of obtaining a biological sample comprising at least one cancer cell or cancer-associated cell from said subject, exposing the biological sample to an ionic detergent, a reducing agent, and a non-mammalian polypeptide capable of binding a mammalian protein, to produce a vaccine comprising a solubilized biological sample comprising components from said cancer cell or cancer-associated cell, and a non-mammalian polypeptide capable of binding a mammalian protein, and administering a therapeutically effective amount of said vaccine to said subject, wherein all steps of the method are performed by or under the supervision of a registered medical practitioner having prime responsibility for the clinical care of said subject throughout said method.

In an embodiment, the method for treatment or prevention is a course of treatment or prevention comprising multiple steps of administering said vaccine to said patient.

In a further embodiment, one or more step(s) of the method is conducted by a person or persons under the supervision of said medical practitioner. In an embodiment the collective steps of the method are performed by a plurality of individuals.

In an embodiment, the collective steps of the method are performed at multiple locations. In one embodiment, the step of obtaining a biological sample from said subject is conducted at a different location to said exposing step.

In other embodiments, the method for the treatment or prevention of cancer in a human subject further comprises additional steps described herein for the production of said vaccine, or the production of a pharmaceutical composition comprising said vaccine.

Vaccine Booster

The inventors have surprisingly found that the administration of compositions comprising mesenchymal stem cells can enhance the therapeutic efficacy of some pharmaceutical compositions, in particular, vaccines.

Accordingly, the present invention provides a method of treating or preventing a disease or disorder in a subject, the method comprising administering to said subject a therapeutically effective amount of a vaccine specific for said disease or disorder, and a composition comprising mesenchymal stem cells.

The mesenchymal stem cells (MSCs) may originate from any tissue where MSCs are found, including, but not limited to, bone marrow, skeletal muscle, skin, connective tissue, and adipose tissue. By originate is meant the tissue type that the MSCs are isolated from for use in the methods or compositions of the present invention. In a particular embodiment, the MCSs may originate from bone marrow or adipose tissue. In another embodiment, the MSCs originate from the subject intended to receive the vaccine and the composition comprising the MSCs. In that context, the composition comprising MSCs may be described as autologous. As described below, however, it will be understood that the MSCs may be isolated from a tissue specifically for the purposes of the methods and compositions of the invention, or the MSCs may have previously been isolated from a tissue source in a procedure unrelated to the methods or compositions of the invention. The isolation of MSCs from suitable tissue or the preparation of a composition comprising MSCs may or may not constitute a step or steps of performance of the method of the invention. In another embodiment, the MSCs originate from a different individual of the same species as the subject intended to receive the composition comprising the MSCs. In that context, the composition comprising MSCs may be described as heterologous or allogeneic. In a preferred embodiment, the MSCs originate from a different species to the subject intended to receive the composition comprising the MSCs. In that context, the composition comprising MSCs may be described as xenogeneic.

Compositions comprising MSCs may comprise MSCs initially isolated from a biological sample comprising tissue where MSCs are found, such as described above. The MSCs may be isolated from a biological sample, and then handled, maintained and stored, according to appropriate methods known to those skilled in the art. It would be understood that appropriate methods of isolation, handling, maintenance and storage would be methods that are conducive to the MSCs retaining multipotency. The MSCs may, for example, be used in the method of the present invention immediately after being isolated from a biological sample. Alternatively, the MSCs may go through one or more stages of freezing, and/or passaging in cell culture prior to use. For example, the MSCs isolated from a biological sample may be passaged in cell culture once prior to use in the method, or the MSCs may be isolated from a biological sample and then frozen and thawed prior to use, or the isolated MSCs may be frozen, thawed and then passaged once in cell culture prior to use. The MSCs may, for example, be isolated from a biological sample and passaged in cell culture, then frozen and thawed, and then passaged one or more times in cell culture prior to use. In another example, the MCSs may be isolated from a biological sample and passaged one or more times in cell culture prior to use. It would be understood that passaging involves growing of the MSCs in cell culture media, and is often referred to as expanding, colony expansion, splitting.

Methods for isolating MSCs from biological tissues are known in the art as are methods for in vitro culturing of MSCs are known in the art and have been described in the art, for example, in Gimble, J., Katz, A., & Bunnell, B. (2007). Adipose-derived stem cells for regenerative medicine. *Circ Res,* 100(9), 1249-1260. doi:100/9/1249 [pii] 10.1161/01.RES0.0000265074.83288.09; Soleimani, M., & Nadri, S. (2009). A protocol for isolation and culture of mesenchymal stem cells from mouse bone marrow. *Nature Protocols,* 4(1), 102-106. doi:10.1038/nprot.2008.221.

It would be understood that methods for the isolation of MSCs from a biological sample may not produce a sample that is comprised of only MSCs. The compositions comprising MSCs may comprise cells that are not MSCs, as well as non-cellular components. These non-cellular components and non-MSCs may, for example, have originated from the biological sample that the MSCs were isolated from, or they may, for example, be from buffers, solutions or media used during handling, maintenance, culturing and storage of the MSCs. The cells that are not MSCs may, for example, be from connective tissue, blood, bone marrow, adipose tissue, blood vessels, nervous tissue, muscle tissue and/or stromal tissue. The cells may be adipocytes that may have, for example, been in the biological sample that the MSCs were isolated from. In certain embodiments, the composition comprising the MSCs further comprises adipocytes. The non-cellular components may be, for example, tissue fluid, cell culture media, plasma components, extra-cellular matrix, enzymes, growth factors and cytokines. The non-cellular components may, for example, be components of the serum used during the passaging of the MSCs.

Suitable methods for the preparation of compositions for use in the methods of the invention are also described in patent application entitled "Therapeutic methods and compositions" patent application number PCT/AU2012/001140, filed 21 Sep. 2012, published as WO2013/040649, the contents of which are incorporated herein by reference.

The administration or use of MSCs as described herein may enhance the therapeutic efficacy of any vaccine useful for the treatment or prevention of any disease or disorder.

By therapeutic efficacy is meant the ability of a vaccine to produce the desired effect of the vaccine. Generally, the desired effect of a vaccine is the treatment or prevention of a disease or disorder.

As described herein, the inventors have found that enhanced therapeutic efficacy may be obtained when a subject is administered a vaccine and MSCs. The subject may therefore experience a more beneficial effect(s) by virtue of the method than, for example, the vaccine alone. Any aspect of treatment or prevention, as described herein, may be enhanced by the method of the present invention.

In a particular embodiment of the invention, the vaccine is an anti-cancer vaccine. An anti-cancer vaccine is any vaccine that is useful for the treatment or prevention of a disease or disorder that is cancer.

It would be understood that treatment, in the context of a disease or disorder that is cancer, includes the alleviation of the symptoms associated with a cancer, as well as cancer regression or remission. The treatment may slow, delay or halt the proliferation or metastasis of a cancer, prevent differentiation of a cell line, or reverse the progression of one or more tumours, at least temporarily. The treatment may prevent or delay or retard the recurrence of any cancer after treatment.

It would also be understood that prevention, in the context of a disease or disorder that is cancer, refers to the prevention of the recurrence of all or some of the symptoms associated with a cancer after a remission of said cancer, as well as the prevention of the formation of one or more cancers due to, for example, the metastasis of a cancer. The prevention may prevent morbidity due to one or more cancers, or delay morbidity due to one or more cancers.

In particular embodiments of the present invention, the anti-cancer vaccine comprises solubilized and reduced components of cancer cells or cancer-associated cells. In particular embodiments of the present invention, the anti-cancer vaccine may be any of the vaccines, or made according to the methods, as described herein.

The cancer cells or cancer-associated cells may be from any biological sample obtained from a subject. The biological sample may contain at least one cancer cell from any of the previously mentioned cancers.

In a particular embodiment of the invention, the cancer cells or cancer-associated cells are from the subject intended to receive the vaccine and the composition comprising MSCs. In that context, the vaccine may be described as autologous.

In particular embodiments of the methods of the present invention, both the vaccine and the composition comprising the MSCs that are administered to the subject are autologous. In an embodiment the vaccine is autologous to the recipient subject and the MSCs are allogeneic, in that they originate from a different individual of the same species as the recipient subject. In an embodiment the vaccine is autologous to the recipient subject and the MSCs are xenogeneic, in that they originate from a different species to the recipient subject.

In the methods of the present invention, the vaccine and the composition comprising the MSCs may be administered to the subject at the same time or at different times, or at any time during treatment of the subject. The vaccine and composition comprising MSCs may be administered via the same or different administration routes. The vaccine and composition comprising MSCs may be administered separately or as a single mixture. For example, the vaccine and composition comprising MSCs may be mixed together and administered as a single composition by injection. In another example, the vaccine may be administered orally prior to administering the composition comprising MSCs by injection. In a further example, the vaccine may be administered by injection at a particular site on the body of the subject, and the composition comprising MSCs administered by injection at or near the same site immediately after.

In embodiments where the vaccine is an anti-cancer vaccine, the vaccine and/or the composition comprising MSCs may be administered by injection, either directly into, or in the vicinity of, a tumour.

In the methods of the present invention, one or both of the vaccine and the composition comprising MSCs may be administered to the subject one or more times. The vaccine may, for example, be administered to a subject the same number of times that the composition comprising MSCs is administered to the subject, or fewer times than the composition comprising MSCs is administered to the subject, or more times than the composition comprising MSCs is administered to the subject. For example, the composition comprising MSCs may be administered to the subject every time the vaccine is administered. In another example, the composition comprising MSCs may be administered when the vaccine is administered, and then subsequently administered to the subject one or more times in predetermined intervals after the vaccination. In a further example, if appropriate administration of the vaccine involves a series of administrations, such as two, three, or more vaccinations, the composition comprising MSCs may be administered to a subject at the time of the first administration of the vaccine, but then not administered at the time of the second and third vaccinations.

In embodiments of the invention administration of the vaccine and or the composition comprising MSCs may be either remotely from the site of the tumour or close to the site of the tumor. In preferred embodiments the cells and the vaccine would be administered as closely together as possible. Other embodiments include delivering them in a pattern with one being inside the other. For example, the cells could be administered in a number of spots to form a circle and the vaccine could be administered within the circle.

In embodiments of the invention frequent doses of cells may be administered until the tumor has completely disappeared or a satisfactory result has otherwise been achieved.

In particular embodiments of the methods of the present invention, the vaccine and composition comprising MSCs comprising the MSCs are administered to the subject at the same time. By "same time" is meant within six hours of each other. In this instance, the vaccine may be administered to the subject up to six hours before or after the administration of the composition comprising MSCs. For example, the vaccine may be administered to the subject, followed by administration of the composition comprising MSCs to the subject 5 minutes later. In another example, the composition comprising MSCs may be administered to the subject three hours before administering the vaccine to the subject.

The present invention also provides compositions comprising a vaccine and MSCs.

In a further aspect of the invention, the composition comprises a vaccine that is an anti-cancer vaccine. The vaccine may be any of the anti-cancer vaccines herein described.

In a further aspect the invention also provides kits for use in the methods of the present invention, the kit comprising one agent for the preparation of a composition comprising MSCs and instructions for use of the kit or a component(s) of the kit in a method of enhancing the therapeutic efficacy of a vaccine or a method for the treatment or prevention of cancer.

In one embodiment, the kit further comprises at least one vaccine. In another embodiment, the kit further comprises at least one agent for the preparation of any one of the anti-cancer vaccines as described herein.

In a further embodiment, the kit comprises a vaccine specific for a disease or disorder, and a composition comprising MSCs. In a preferred embodiment, the vaccine specific for a disease or disorder and the composition comprising are housed in separate containers.

The present invention also provides a method for the treatment or prevention of cancer in a subject, the method comprising administering to said subject a composition comprising MSCs. The compositions comprising MSCs used in the method for the treatment or prevention of cancer may be any of the compositions comprising MSCs described herein.

In a particular embodiment, the method further comprises administering to said subject an anti-cancer vaccine. The anti-cancer vaccine may be any of the anti-cancer vaccines herein described.

In a particular embodiment, the anti-cancer vaccine comprises the components of cancer cells and cancer-associated cells from the subject intended to receive the composition comprising MSCs.

In a particular embodiment of the method for the treatment or prevention of cancer, the MCSs may originate from bone marrow or adipose tissue. In an embodiment the MSCs are allogeneic to the recipient subject, in that they originate from a different individual of the same species as the recipient subject. In an embodiment the MSCs are xenogeneic to the recipient subject, in that they originate from a different species to the recipient subject.

In another embodiment, the MSCs originate from the subject intended to receive the vaccine and the composition comprising the MSCs.

As described herein, an anti-cancer vaccine may be autologous to the recipient subject. Alternatively, or additionally, the MSCs in the composition comprising MSCs may be autologous to the recipient subject. In a particular embodiment, both the anti-cancer vaccine and the MSCs, are autologous to the recipient subject, and that subject is under the primary care of a single medical practitioner for the course of the treatment.

Any of the biological samples used in the present invention may be collected from a subject under the clinical care of a medical practitioner by, for example, a medical practitioner or a health care professional. A medical practitioner may be any person that is registered, authorized or certified under law to practice medicine independently. A health care professional may be any person that is permitted, authorized, registered or certified to collect a biological sample from a subject either independently or under the supervision of a medical practitioner. For example, the health care professional may be a registered or enrolled nurse, or a medical practitioner's assistant or a clinical assistant. It would be understood that the biological sample may, for example, be collected during routine out-patient procedures that would ordinarily be carried out on a subject with cancer who is under the clinical care of a medical practitioner.

In embodiments of the present invention, the methods described herein permit the production of a therapeutic product of human origin which satisfies the requirements of for exclusion from regulation by the Australian Therapeutic Goods Administration (TGA) of goods manufactured and used in medical practice. The TGA is part of the Australian government Department of Health and Human Aging and is responsible for regulating medicines and medical devices. Under the relevant provisions, human cells and tissues or therapeutic goods manufactured therefrom, may be excluded from the requirement of inclusion in the Australian Register of Therapeutic Goods (ARTG) and from compliance with TGA legislation. The provision applies to human cells and tissues that are collected from a patient who is under the clinical care and treatment of a medical practitioner registered under a law of a State or an internal Territory; and manufactured by that medical practitioner, or by a person or persons under the professional supervision of that medical practitioner, for therapeutic application of a single indication and in a single course of treatment of that patient by the same medical practitioner, or by a person or persons under the professional supervision of the same medical practitioner. The relevant provision thus requires that the product is for autologous use only.

Consistent with those requirements, the present invention provides a method for the treatment or prevention of cancer in a human subject, the method comprising the steps of: obtaining a biological sample comprising at least one cancer cell or cancer-associated cell from said subject, exposing the biological sample to an ionic detergent, a reducing agent, and a non-mammalian polypeptide capable of binding a mammalian protein, to produce an anti-cancer vaccine comprising a solubilized biological sample comprising components from said cancer cell or cancer-associated cell, and a non-mammalian polypeptide capable of binding a mammalian protein, and administering a therapeutically effective amount of said vaccine to said subject; and obtaining a biological sample comprising MSCs from said subject, isolating MSCs from the biological sample and preparing a composition comprising MSCs, and administering a therapeutically effective amount of said composition comprising MSCs to said subject; wherein all steps of the method are performed by or under the supervision of a registered medical practitioner having prime responsibility for the clinical care of said subject throughout said method.

The present invention also provides a method for enhancing the efficacy of a vaccine in a human subject, the method comprising the steps of: administering a therapeutically effective amount of a vaccine to said subject; and obtaining a biological sample comprising MSCs from said subject, isolating MSCs from the biological sample and preparing a composition comprising MSCs, and administering a therapeutically effective amount of said composition comprising MSCs to said subject; wherein all steps of the method are performed by or under the supervision of a registered medical practitioner having prime responsibility for the clinical care of said subject throughout said method.

In particular embodiments, one or more step(s) of the methods are conducted by a person or persons under the supervision of said medical practitioner. In an embodiment, the collective steps of the methods are performed by a plurality of individuals.

In an embodiment, the collective steps of the methods are performed by a plurality of individuals, all of which are under the supervision of a registered medical practitioner having prime responsibility for the clinical care of said subject throughout said method.

In an embodiment, the collective steps of the methods are performed at multiple locations. In one embodiment, the steps of obtaining biological samples from said subject are conducted at a different location or locations to one or more of said administering steps.

Compositions, Vaccines and Medicaments

The present invention provides vaccines for the treatment or prevention of cancer produced by any of the previously discussed methods. The vaccines may also be used for the manufacture of other medicaments for treatment of prevention of cancer. In another embodiment, the invention also provides pharmaceutical compositions comprising the vaccine of the present invention.

In aspects of the invention relating to vaccines for the treatment or prevention of cancer, the pharmaceutical composition, vaccines and medicaments of the invention comprise at least solubilized and reduced components of a cancer cell or cancer-associated cell and a non-mammalian polypeptide capable of binding a mammalian protein.

As described herein the inventors have also surprisingly found that the administration of compositions comprising mesenchymal stem cells (MSCs) can enhance therapeutic effect of pharmaceutical compositions, in particular of vaccines. The invention herein therefore also provides the use of a composition comprising MSCs for enhancing therapeutic efficacy of a vaccine. In a preferred embodiment the vaccine is an anti-cancer vaccine. In aspects of the invention associated with therapeutic use of MSCs, such as for enhancing the therapeutic efficacy of a vaccine or for the treatment or prevention of cancer, a composition of the invention comprises at least MSCs.

The pharmaceutical compositions, vaccines and medicaments of the present invention may further comprise a pharmaceutically acceptable carrier, adjuvant, excipient and/or diluents. For preparing the pharmaceutical compositions, vaccines and medicaments, inert, pharmaceutically acceptable carriers can be either solid or liquid. Liquid form preparations include solutions, suspensions and emulsions, for example water or water-propylene glycol solutions for parenteral injection. Also included are solid form preparations that are intended to be converted, shortly before use, to liquid form preparations for either oral or injection administration. Such liquid forms include solutions, suspensions and emulsions. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

The carriers, diluents, excipients and adjuvants must be "acceptable" in terms of being compatible with the other ingredients of the composition, vaccine or medicament, and are generally not deleterious to the subject thereof. Non-limiting examples of pharmaceutically acceptable carriers or diluents are demineralised or distilled water; saline solution; vegetable based oils such as peanut oil, safflower oil, olive oil, cottonseed oil, maize oil; sesame oils such as peanut oil, safflower oil, olive oil, cottonseed oil, maize oil, sesame oil, *arachis* oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxylpropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrolidone; agar; gum tragacanth or gum *acacia*, and petroleum jelly. Typically, the carrier or carriers will form from about 10% to about 99.9% by weight of the composition, vaccine or medicament.

The pharmaceutical compositions, vaccines and medicaments of the present invention may be in a form suitable for administration by injection (e.g. for parenteral administration including subcutaneous, intramuscular or intravenous injection) or by oral administration (such as capsules, tablets, caplets, and elixirs, for example). For administration as an injectable solution or suspension, non-toxic parenterally' acceptable diluents or carriers can include, Ringer's solution, isotonic saline, phosphate buffered saline, ethanol and 1,2 propylene glycol. Methods for preparing parenterally administrable pharmaceutical compositions, vaccines and medicaments are apparent to those of ordinary skill in the art, and are described in more detail in, for example, Remington's Pharmaceutical Science, 15th ed., Mack Publishing Company, Easton, Pa.

For oral administration, some examples of suitable carriers, diluents, excipients and adjuvants include peanut oil, liquid paraffin, sodium carboxymethylcellulose, methylcellulose, sodium alginate, gum *acacia*, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl stearate which delay disintegration. Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum *acacia*, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, *arachis* oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

Supplementary active ingredients such as adjuvants or biological response modifiers can also be incorporated into the pharmaceutical compositions, vaccines and medicaments of the present invention.

Any suitable adjuvant may be included in the pharmaceutical compositions, vaccines and medicaments of the present invention. For example, an aluminium-based adjuvant may be utilised. Suitable aluminium-based adjuvants include, but are not limited to, aluminium hydroxide, aluminium phosphate and combinations thereof. Other specific examples of aluminium-based adjuvants that may be utilised are described in European Patent No. 1216053 and U.S. Pat. No. 6,372,223. Other suitable adjuvants include Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminium salts such as aluminium hydroxide gel (alum) or aluminium phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A; oil in water emulsions including those described in European Patent No. 0399843, U.S. Pat. No. 7,029,678 and PCT Publication No. WO 2007/006939; and/or additional cytokines, such as GM-CSF or interleukin-2, -7, or -12, granulocyte-macrophage colony-stimulating factor (GM-CSF), monophosphoryl lipid A (MPL), cholera toxin (CT) or its constituent subunit, heat labile enterotoxin (LT) or its constituent subunit, toll-like receptor ligand adjuvants such as lipopolysaccharide (LPS) and derivatives thereof (e.g. monophosphoryl lipid A and 3-Deacylated monophosphoryl lipid A), muramyl dipeptide (MDP) and F protein of Respiratory Syncytial Virus (RSV).

Dosages and Routes of Administration

The pharmaceutical compositions, vaccines and medicaments of the present invention may be administered to a subject by standard routes including, but not limited to, injection and oral. In some embodiments, they may be administered to a subject in isolation or in combination with other additional therapeutic agent(s). In such embodiments the administration may be simultaneous or sequential.

The pharmaceutical compositions, vaccines and medicaments of this invention may also be delivered by intramuscular, subcutaneous and/or intradermal injections. They may be delivered by injection near a lymph node or by injection directly into a tumour.

In general, the pharmaceutical compositions, vaccines and medicaments of the present invention can be administered in a manner compatible with the route of administration and physical characteristics of the subject (including health status) and in such a way that the desired effect(s) are induced (i.e. therapeutically effective, immunogenic and/or protective). For example, the appropriate dosage may depend on a variety of factors including, but not limited to, a subject's physical characteristics (e.g. age, weight, sex), whether the composition, vaccine or medicament is being used as single agent or adjuvant therapy, the progression (i.e. pathological state) of the cancer, or other disease, disorder or condition, being treated, and other factors readily apparent to those of ordinary skill in the art.

Various general considerations when determining an appropriate dosage of compositions, vaccines and medicaments are described, for example, in Gennaro et al. (Eds), (1990), "Remington's Pharmaceutical Sciences", Mack Publishing Co., Easton, Pa., USA; and Gilman et al., (Eds), (1990), "Goodman And Gilman's: The Pharmacological Bases of Therapeutics", Pergamon Press.

Typically, in treatment applications, the treatment may be for the duration of the condition afflicting the subject. Further, it will be apparent to one of ordinary skill in the art that the optimal quantity and spacing of individual dosages can be determined by the nature and extent of the disease state or condition being treated, the form, route and site of administration, and the nature of the particular subject being treated. Optimum dosages can be determined using conventional techniques.

Some embodiments of the present invention may involve administration of the pharmaceutical composition, vaccine or medicament in multiple, separate doses. Accordingly, the methods for treatment described herein encompass the administration of multiple separated doses to a subject, for example, over a defined period of time. Accordingly, in some embodiments the methods include administering a priming dose, which may be followed by a booster dose. The booster may be for the purpose of re-vaccination. In various embodiments, the pharmaceutical composition, vaccine or medicament is administered at least once, twice, three times or more.

The pharmaceutical compositions, vaccines and medicaments of this invention may also be useful in combination (administered together or sequentially) with one or more of other treatments for the disease, disorder or condition. For example where the condition being treated is cancer the compositions, vaccines and methods of this invention described herein may be useful in combination (administered together or sequentially) with one or more of anticancer treatments such as radiation therapy, and/or one or more anti-cancer agents selected from the group consisting of cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™ (4~[2-[4-[(11R)-3,10-dibromo-8-chloro-6,11-dihydro-5H-benzo[5,6]cyclohepta[1,2-b]pyridin-11-yl-]-1-piperidinyl]-2-oxoethyl]-1-piperidinecarboxamide, or SCH 66336 from Schering-Plough Corporation, Kenilworth, N.J.), tipifamib (Zamestra® or R115777 from Janssen Pharmaceuticals), L778.123 (a famesyl protein transferase inhibitor from Merck & Company, Whitehouse Station, N.J.), BMS 214662 (a famesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, Cytoxan, and gemcitabine.

Subjects

The subject is any individual in respect of which any of the methods of treatment or vaccine production or administration are performed. A subject may also be referred to herein as a patient. Typically the subject is under the clinical care of a medical practitioner or veterinary practitioner.

Typically, in aspects of the invention pertaining to vaccines comprising solubilised components of cancer cells or cancer associated cells, or in aspects of the invention pertaining to the use of mesenchymal stem cells in therapy of cancer, the subject is an individual having cancer who, if human is under the clinical care of a medical practitioner or if non-human is under the clinical care of a veterinary practitioner. The subject may be the same individual from which the biological sample comprising the cancer cells was obtained.

Typically, in aspects of the invention pertaining to the use of mesenchymal stem cells to enhance the therapeutic effect of a vaccine the subject is an individual having a disease or disorder or is at risk of the disease or disorder which may be treated or prevented by the vaccine. Typically, in aspects of the invention pertaining to the use of mesenchymal stem cells to inhibit the progression of cancer cells, the subject is an individual having cancer. The subject to which the composition of the invention is to be administered may be the same individual from which the MSCs originate, or may be a different individual of the same species, or may be an individual of a different species from which the MSCs originate. Typically, the subject is under the clinical care of a medical practitioner or veterinary practitioner.

The subject may be human or may be a non-human such that reference to a subject or individual means a human or a non-human, such as an individual of any species of social, economic or research importance including but not limited to members of the classifications of ovine, bovine, equine, porcine, feline, canine, primates, rodents, especially domesticated members of those classifications, such as sheep, cattle, horses and dogs.

It will be appreciated by persons of ordinary skill in the art that numerous variations and/or modifications can be made to the present invention as disclosed in the specific embodiments without departing from the spirit or scope of the present invention as broadly described. The present embodiments are, therefore, to be considered in all respects as illustrative and not restrictive.

The present invention will now be described with reference to specific examples, which should not be construed as in any way limiting.

EXAMPLES

Example 1

Preliminary Vaccine Trials and Dosing Studies

Materials and Methods

Cell Culture

Rat glioma cells (9 L) cell were cultured in Basal Medium Eagle (BME) supplemented with 10% (v/v) foetal calf serum and 0.03% (w/v) L-glutamine until approximately 90% confluent. The cells were washed in PBS, trypsinized and collected from the flask. The cells were then washed once with serum free BME, counted and resuspended at a concentration of $10 \times 10^6$ cells per ml for injection into rats.

Induction and Biotin Perfusion of Tumours for Vaccine Production

Rats were injected with $1\times10^6$ 9L glioma cells (100 μl) under the skin in the flank and a tumour allowed to establish. Once the tumour reached approximately 1 cm³ the rats were perfused with biotin according to the following method:

Rats were anaesthetised and once asleep taped down, and the belly and chest area shaved. An incision was made under the sternum so the heart was visible and 0.5 ml of heparin was directly injected into the heart to prevent clotting. A blunt perfusion needle was then inserted into the right atrium of the heart and main blood supply below the heart clamped and cut below. Saline was the pumped through the rat for 20 mins. After this 60 ml of buffer containing 0.05M Tris, 0.15M NaCl, pH 7.6 was pumped through the rat followed by 20 mg of Biotin-ss (Thermo) in PBS. Once the biotin-PBS had passed through, the rat was flushed through with a further 60 ml of buffer containing 0.05M Tris, 0.15M NaCl, pH 7.6. Biotin perfused tumours were then removed from the animal and later used to prepare the vaccine.

Induction of Tumours in a Donor Rat

An initial donor rat was injected with $1\times10^6$ 9L glioma cells under the skin in the flank and a tumour allowed to establish. Once a tumour reached a size of approximately 0.5 cm³, the rat was euthanized and the tumour aseptically removed. The tumour was then chopped up finely to obtain small pieces of tumour approximately 1 mm×1 mm in size. These tumour pieces were kept on ice in serum-free BME media until rats were ready for implantation.

Rechallenging Rats in the Vaccine Trial

For flank rechallenge experiments, rats were anesthetised and injected with $1\times10^6$ 9L Glioma cells in the flank.

For brain rechallenge experiments, a tumour from a donor rat was harvested and cut into small approximately 1 mm pieces and stored cold in serum free BME until use. Rats had a small hole drilled in the left side of brain and a small piece of tumour implanted and sealed with bone wax.

Rats were monitored for recovery and treated with xylocaine at the site tumour implantation. Rats with brain tumour implants were monitored daily for signs of distress, Initial Vaccine Trial Every 1 gram of perfused tumour was homogenised and solubilised in 40 ml of 0.05M Tris, 0.15M NaCl and 1% SDS buffer (ph7.6) with a protease inhibitor (Roche). Tumour lysate was then spun down at 10,000 rpm for 30 mins at room temperature. The supernatant was collected and pellet discarded. Supernatant was then run over a pre equilibrated streptavidin (TRIS-NACL-SDS) column (Thermo scientific) at 2 parts supernatant: 1 part column, and allowed to incubate for 1 hr. The column was washed with 5× column buffer followed by elution with 1 column volume of Tris-Nacl-SDS buffer with 50 mM DTT (incubated for 1 h). 2 ml of eluted vaccine proteins were precipitated overnight with 20 mls of ice cold acetone and incubated overnight at −20° C. The follow day samples were spun down at 10,000 rpm for 30 mins and supernatant discarded. Pellet was allowed to dry and resuspended in 200 μl sterile PBS.

Each 200 μl batch was used as an individual vaccine for each rat and mixed 1:1 with Freund's Incomplete Adjuvant. Rats received vaccine or FIA with PBS intraperitoneally (i.p), then received a booster shot after 3 weeks. They were then challenged with $1\times10^6$ 9L cells in the flank and this was termed day zero. Animals had tumours measured by calipurs 3 times per week. Tumour size was measured by the equation (width²× Length)/2.=cm³.

Vaccine Dosing Trial

Vaccines were prepared by the same method as the initial vaccine trial. A control group of rats (n=8) received 2 vaccinations of PBS/FIA i.p. Vaccine groups of rats were given either 1 (n=8), 2 (n=9) or 3 (n=9) doses of vaccine i.p. A fourth vaccine group of rats (n=8) received 2 doses of vaccine subcutaneously. All groups were challenged with $1\times10^6$ 9L glioma cells in the flank 2 weeks after the last vaccination.

Tumour Rechallenge Trial

Rats from group 1 or 2 (above) that survived the vaccine dosing trial (N=9 total) were split into 2 groups. Group 1 (N=4) were rechallenged with $1\times10^6$ 9L glioma cells in the flank along with untreated controls (n=10). Group 2 (n=5) received a small piece of tumour in the brain along with untreated controls (n=6).

Calculation of Survival Rates and Survival Times

For analysis of the results, a cured rat was one in which the tumour resolved and disappeared. Cure rates were defined by how many per group were cured (e.g. 6/10=60%).

Survival rates were defined in days to euthanasia. For ethical reasons rats were euthanized once the tumours reached an approximate size of 13.5 cm³. The mean survival time (days) was calculated for each group. 'Cured' or "in Remission" rats are assigned a value of 100 days. Survival curves were plotted to measure for significance between groups.

Results

Figure 2:
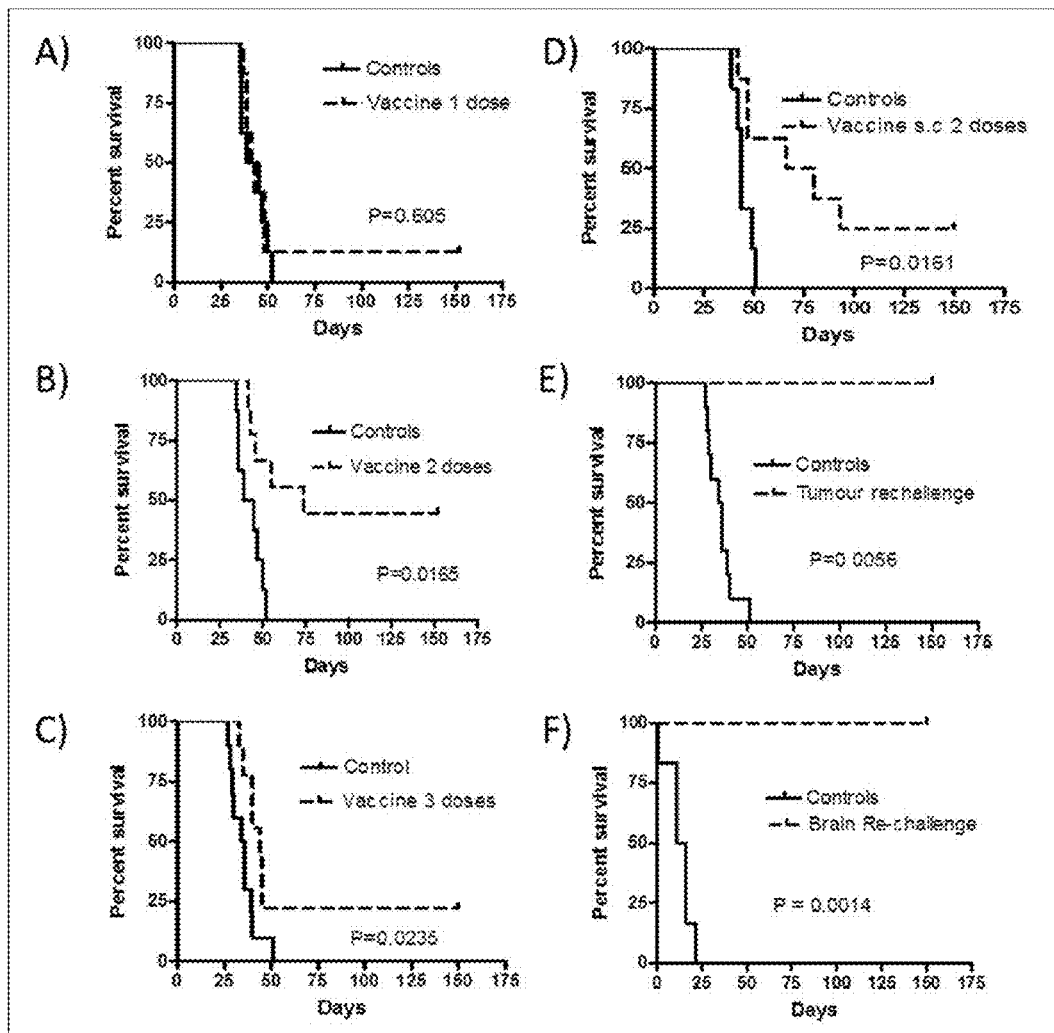
FIG. 2 shows the results from the vaccine dosing trial and tumour rechallenge trial. A) Survival of control rats (n=8, Solid line) v rats that received a single vaccination dose (n=8, dashed line). B) Survival of control rats (n=8; Solid line) v rats that received two vaccinations (n=9, dashed line). C) Survival of control rats (n=8, Solid line) v rats that received three vaccination doses (n=9, dashed line). D) Survival of control rats (n=8, Solid line) v rats that received two vaccination doses S.C. (n=8, dashed line). E) Survival of control rats (n=8, Solid line) v rats that were rechallenged (n=4) with tumour cells in the flank. F) Survival of control rats (n=8, Solid line) v rats that were rechallenged (n=5) with tumour in the brain.

The initial vaccine trial comprised rats treated with 2 doses of 9L glioma vaccine or adjuvant to determine the safety and efficacy of the vaccine. The rats showed no adverse effects to the vaccination other than minor swelling at the vaccination site. Two of the three rats in the vaccine treated group developed tumours, however one of these resolved over time and by day 58 post-engraftment had disappeared (FIG. 1A). Two rats were considered "in remission" or "Cured" after surviving beyond 100 days and were kept for rechallenge in the acquired immunity experiments (FIGS. 2 E and F). By contrast, in control adjuvant vaccinated rats the average tumour progression time until ethical endpoint was 35 days (FIG. 1B). Overall there was a significant survival advantage in the vaccinated group compared to adjuvant alone (P<0.05).

After the success of the initial vaccine trial, dosing studies were performed to see if 1, 2 or 3 shots (i.p.) of vaccine was optimal. Remission rates were highest in rats receiving 2 doses compared to 1 or 3 doses (FIG. 2). Both 2 and 3 doses gave a significant extended survival time when compared to control, but a single dose did not. There was no extension of mean survival time between 2 doses of vaccine i.p compared to 2 doses of vaccine s.c. so either vaccination route could be used.

Rats which went into remission in the vaccine dosing trial (n=9) were split into 2 groups and rechallenged in the either the brain (n=−4) or the flank (n=5) (FIGS. 2E and F). All of these rats showed complete immunity to tumour progression when challenged in both the brain and the flank, suggesting acquired immunity and that the immune system may have been working across the blood brain barrier.

Figure 3:
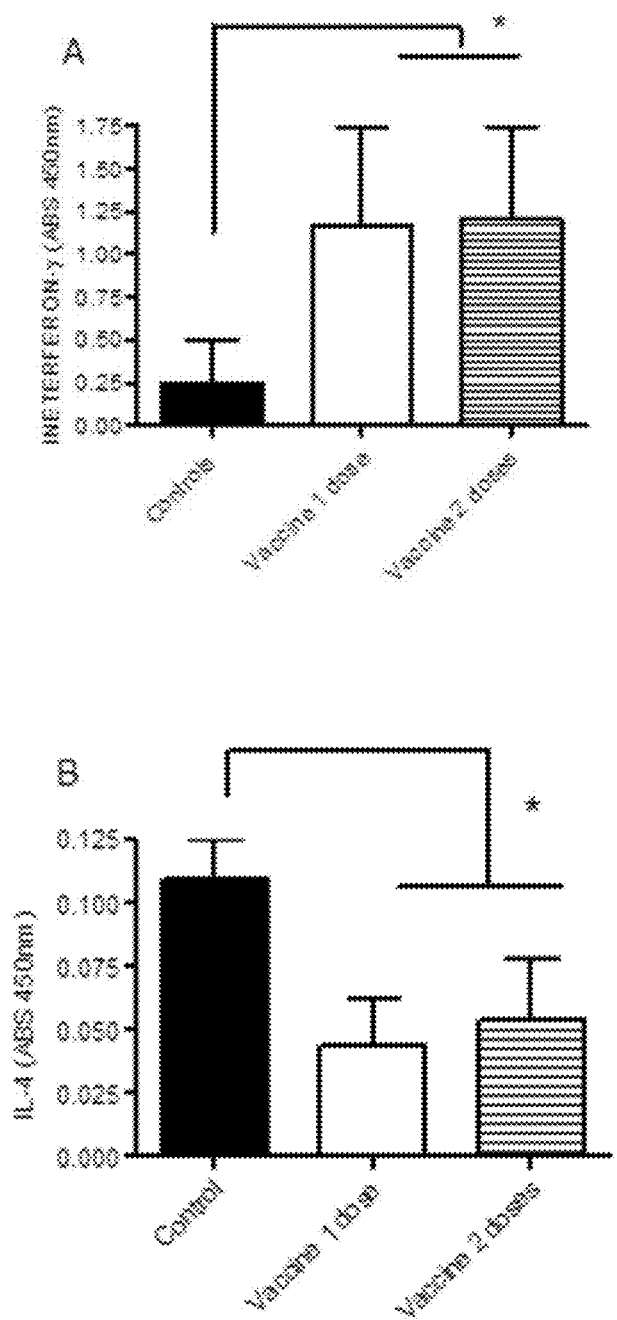
FIG. 3: A) Interferon-γ levels in controls, single vaccine dose or 2 dose treated rats 21 days post tumour challenge. B) IL-4 levels in controls, single vaccine dose or 2 dose treated rats 21 days post tumour treatment. *=p<0.05.

Cytokine analysis was also performed and results are presented in FIG. 3 which shows the up regulation of interferon-γ (A) in vaccinated rats compared to control (adjuvant control), whilst FIG. 3(B) shows a significant down regulation of IL-4 in vaccinated rats compared to control. There was no significant difference in interferon-γ or IL-4 levels in rats receiving one or 2 vaccinations.

The cytokine INF-γ is a critical immune system component of the anti-tumour response. INF-γ together with lymphocytes not only provide protection against tumour development but also assist to sculpt the immunogenic phenotype of tumours for presentation as a "cancer immunoediting" process. Taken together the cytokine results suggest that the vaccine initiates a specific and effective immune anti-tumour response. As described herein, in cured rats interferon γ levels go down again as tumour resolves.

Preliminary Analysis of Vaccines

Figure 4:
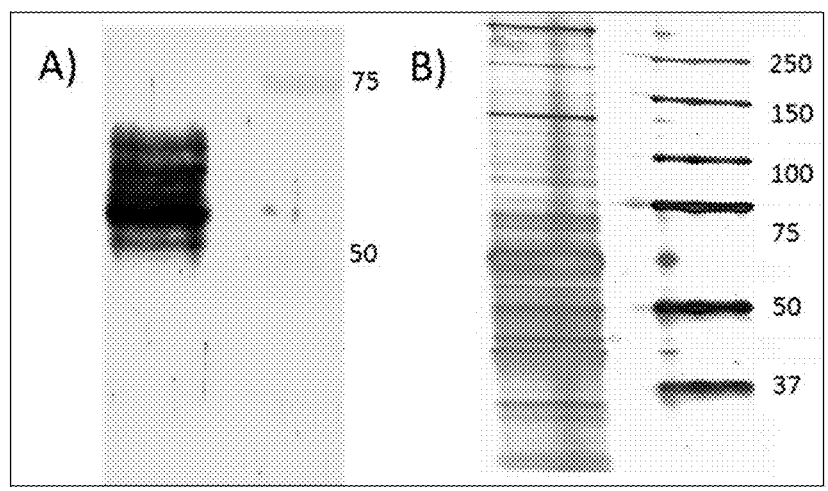
FIG. 4 shows the results obtained from a preliminary analysis of the protein composition of the initial vaccines. A) Vaccinated rat serum reactivity to streptavidin in the vaccine only (no serum reactivity to tumour proteins). B) A silver stained SDS-PAGE gel profile of a typical rat vaccine.

Vaccines used and serum collected from rats in the initial vaccine trials were analysed by SDS-PAGE and western blotting. It was shown that western blot analysis of the vaccines using the serum from the vaccinated rats produced a common 5 or 6 bands between 50 to 75 Kda, which were later proven to be fragments of streptavidin (FIG. 4A). Experiments using different columns to make the vaccines demonstrated, that varying amounts of streptavidin was leeching off the columns.

A sample of unperfused tumour lysate was purified using a streptavidin column to produce the complex banding pattern seen in FIG. 4B. This suggested that streptavidin may have been selecting the vaccine proteins, and could possibly be doing so by RYD or RGD sites on the tumour proteins. Additional experiments using up to 10% SDS in the tumour extraction buffer still yielded a similar complex vaccine profile when unperfused tumour lysates were purified using a streptavidin column, which suggested a high level of affinity between the tumour proteins and streptavidin, and motivated further analysis.

Example 2

Vaccine Components Trials

Materials and Methods
Preparation and Vaccination—Streptavidin (50 μg) Only Vaccine (Streptavidin)

A streptavidin vaccine was prepared by solubilising 300 μg streptavidin (Calbiochem) in buffer containing 1% SDS (w/v), 0.05M Tris, 0.15M NaCl pH 7.6. The soluble streptavidin was precipitated overnight with 1 ml acetone at −20° C. The next day, the sample was spun @ 10,000 rpm for 30 mins to pellet the precipitate. The precipitated streptavidin was then resuspended in 600 μl of PBS and mixed with 600 μl of FIA (Sigma) for vaccination of 6 rats (0.2 ml per vaccination).

Preparation and Vaccination—Reduced Tumour Protein Vaccine (R-Lysate)

Sections of 6 different induced 9L Glioma tumours were collected, weighed (1 gram) and homogenized in 40 ml of buffer containing 1% SDS (w/v), 0.05M Tris, 0.15M NaCl pH 7.6, and protease inhibitor (Roche). The tumour lysate was spun down at 10,000 rpm for 30 min and the soluble tumour lysate collected. The proteins in 2 ml of this lysate were reduced by adding 20 mM TCEP (Sigma) for 2 hours and then precipitated by adding 40 ml of acetone and incubating overnight at −20° C. The next day, the sample was spun down to precipitate the proteins at 10,000 rpm for 30 mins. The precipitate was resuspended in 1.2 ml of PBS and mixed with 1.2 ml of FIA (Sigma) for vaccination of 6 rats (0.3 ml per vaccination).

Preparation and Vaccination—Reduced Tumour Protein+Streptavidin (50 μg) Vaccine (Vaccine (50))

2 ml of tumour lysate, prepared as per the reduced tumour protein vaccine above, was mixed with 300 μg of streptavidin (Calbiochem) and incubated for another 2 hours, before being precipitated overnight with 40 ml of acetone at −20° C. The next day, the sample was spun down to precipitate the proteins at 10,000 rpm for 30 mins. The precipitate was then resuspended in 1.2 ml of PBS, and mixed with 1.2 ml of FIA (Sigma) for vaccination of 6 rats (0.3 ml per vaccination).

Vaccine (100)

A high streptavidin dose vaccine (reduced tumour protein+streptavidin (100 μg) vaccine) was made by the same method as above, but 600 μg of streptavidin was added to 2 ml of the reduced lysate.

Controls

Control rats received FIA/PBS in a 300 μl dose (n=5). All groups received a secondary vaccination 3 weeks later.

Streptavidin ELISA

The reactivity to streptavidin of serum collected from rats involved in the vaccine components trial was measured via ELISA. Streptavidin (Calbiochem) was coated on ELISA plates (NUNC) at a concentration of 10 μg/ml in 0.1 M NaHCO$_3$ overnight at 4° C. Plates were blocked the next day in 3% BSA in PBS for 1 hr at 37° C. Rat serum was diluted 1:1000 in 1% BSA/PBS and incubated on plate at 37° C. for 1 hr. The plate was then washed 4 times with PBS/0.05% tween and then plate incubated with a goat anti-rat-HRP antibody (Sigma) at a 1:2000 dilution in 1% BSA/PBS for 1 hour at 37° C. Plates were washed again and then substrate added for 10 minutes before being stopped. Absorbance was read at 480 nm.

Cytokine Analysis

Cytokine analysis of serum collected from rats in the vaccine components trial was performed initially using 2 broad screening methods. The rat cytokine bioplex (Biorad) and the Rat proteome Profiler™ array (R and D systems) were used according to manufactures instructions for initial rat serum screens to sample a wide range of cytokines. Rat serum samples were also screened using ELISA for rat C-Reactive protein (BD), CINC-2 (R and D systems), ICAM (R and D systems), IL-4(R and D systems), TNF-α (R and D Systems), INF-γ (Bender systems) according to the manufactures instructions.

Flow Cytometric Blood Assay

To assess the levels of Natural Killer (NK), CD4+, CD8+ T cells, B-cell, Lymphocyte, neutrophil and monocyte levels in the peripheral blood of rats in the vaccine components trial, a flow cytometric assay was developed. A sample of blood from test rats was collected into a 0.5 ml EDTA tube to prevent clotting. For each test, 25 μl of blood was added to a Trucount™ tube (BD Pharmingen) and then stained with rat T/B/NK cell cocktail (BD Pharmingen), rat CD8a PE, rat CD4 (domain 1) FITC and rat CD45 PE/Cy7 (Biolegend) for 15 minutes at room temperature. Samples were then lysed using 10 mM Tris and ammonium chloride buffer (pH 7.4). Multiple cell populations were analysed using the following gating strategy. All cell subsets were gated as CD45 positive, monocytes, neutrophils and lymphocytes were then analysed by FSC v SSC. T4 (CD4) cells CD45/CD3/CD4 positive, T8 (CD8) cells CD45/CD3/CD8 positive, NK cells (CD45+/CD3−/CD161a+) and B Cells CD3+/CD45+/CD45RA+.

Cell numbers per μl were calculated as follows:

$$\frac{\text{Cell number}}{25 \ \mu l} \times \frac{\text{Bead number}}{\text{Bead count}}$$

Results (Vaccine Component Study)

Figure 5:
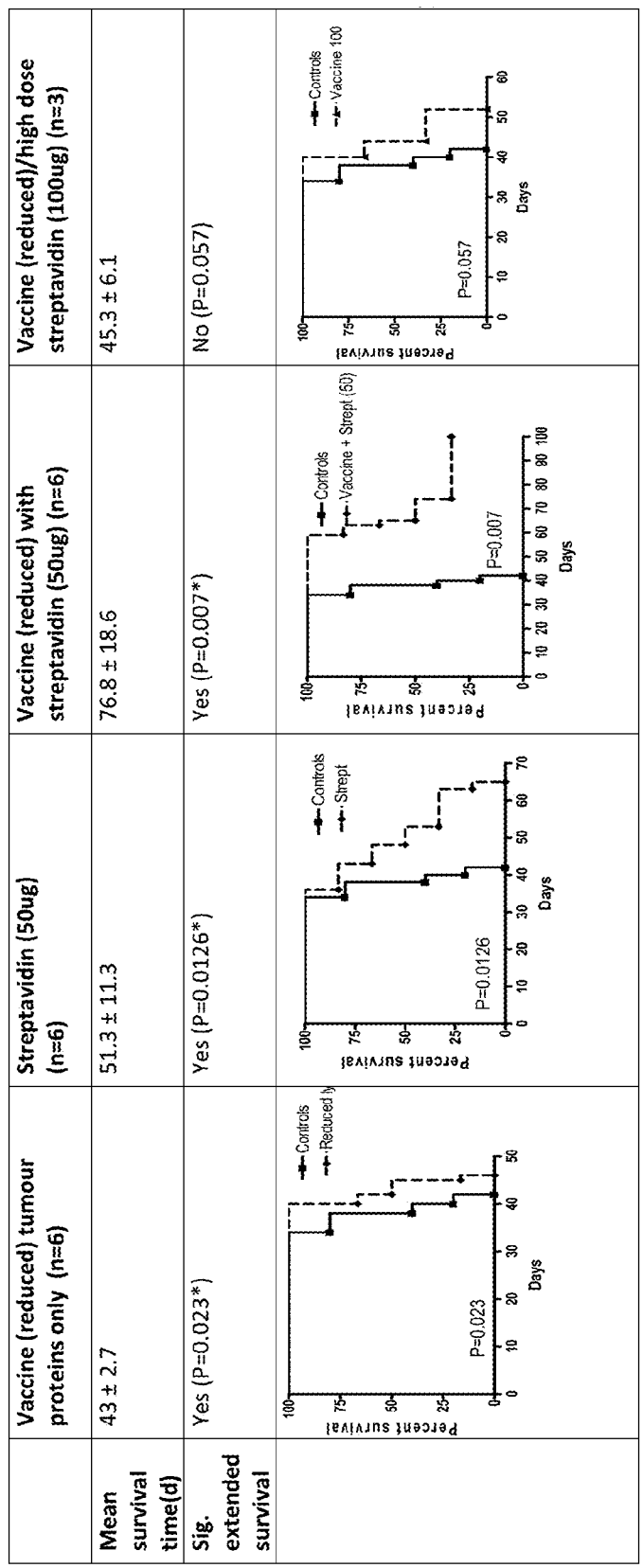
FIG. 5 shows the survival rates of the rats included in the vaccine components trial. Compares survival time (days) and significant extended survival of the four vaccinated groups. The control group (n=5) had a survival time of 38.4±2.9.

In the vaccine components trial, controls rats treated with FIA/PBS survived an average 38 days after being challenged with 9L cells. As can be seen in FIG. 5 and Table 1, the reduced tumour protein vaccine (R-Lysate) group average survival time was 43 days. This was only 5 days more than that the control rats, but this was significant in terms of survival. The streptavidin (50 µg) only vaccine group survived an average of 15 days longer than control rats and showed a significant extended survival on curve (FIG. 5 and Table 1). The reduced tumour protein+streptavidin (50 µg) (vaccine (50)) induced remission in 2 out of 6 rats. The average survival time in this group was double that of the control rats, and an average 25 days longer survival time than the next best group (streptavidin only).

Increasing the dose of streptavidin (100 µg) in the reduced tumour protein+streptavidin (vaccine (100)) decreased the mean survival time dramatically and nullified any remissions.

Figure 6:
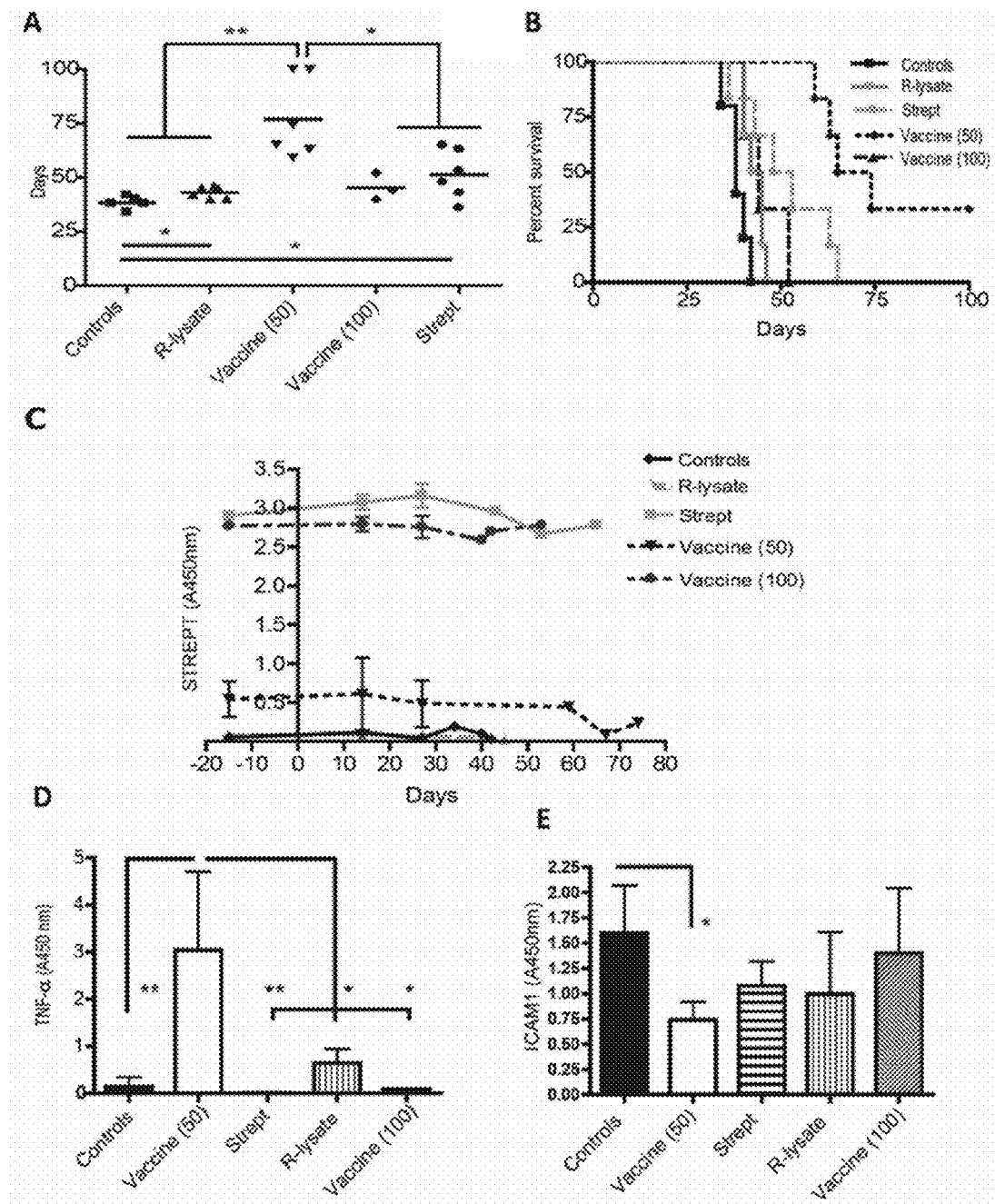
FIG. 6: Vaccine of low dose streptavidin linked to reduced proteins prolongs survival and induces remission, production of streptavidin antibodies, and TNF-α. Parameters for 4 different vaccine types and adjuvant controls were compared: R-lysate: reduced lysate without streptavidine; Vaccine (50): reduced lysate linked with 50 µg streptavidin; Vaccine (100): reduced lysate linked with 100 µg streptavidin; Strept: 50 µg streptavidin alone. A. survival times; B. Survival curves plotted as percentage surviving over time; C. Serum streptavidin antibody levels where Day 0 is the day of engraftment (measured by ELISA); D. Serum TNF-α levels at day 21 post-engraftment; E. Serum ICAM1 levels at day 21 post-engraftment. TNF-α and ICAM1 measured by ELISA. *: P<0.05; **: P<0.001.
Figure 7:
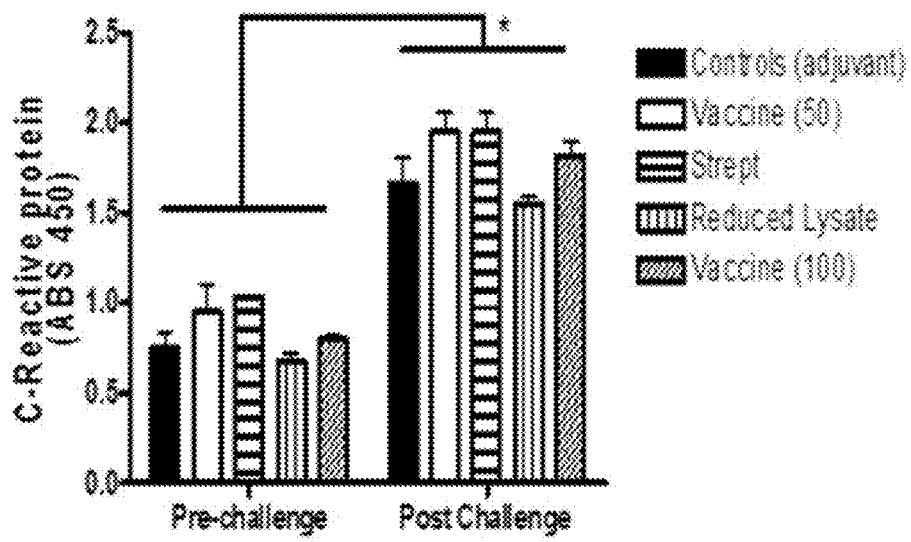
FIG. 7: A) C-reactive protein levels post vaccination/pre-tumour challenge and 21 days post tumour challenge. B) CINC-1 serum levels at endpoint. *=p<0.05
Figure 7:
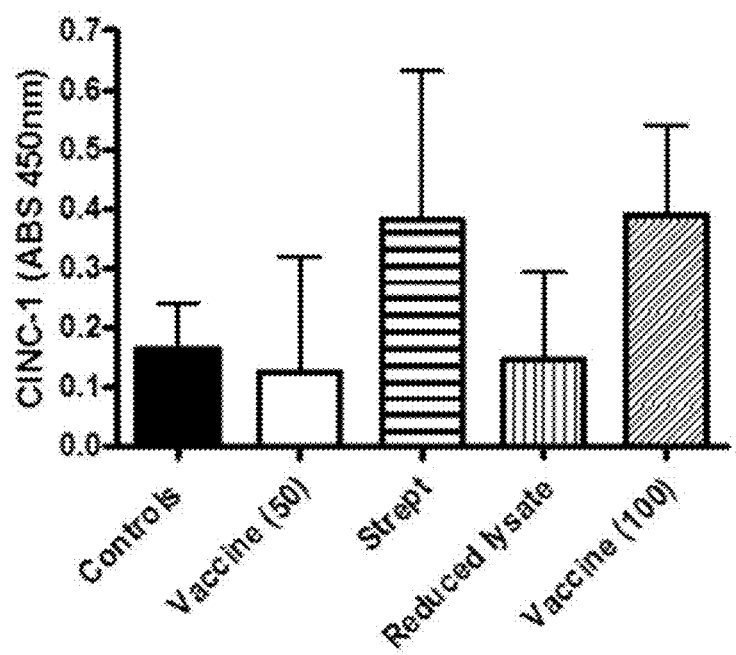

The streptavidin reactivity and cytokine analysis data collected from the vaccine components trial is summarised in FIG. 6, FIG. 7 and Table 1. Serum antibodies to streptavidin were not evident in any of the reduced tumour protein vaccine (R-Lysate) groups (see FIG. 6C). Interestingly, rats vaccinated with streptavidin alone showed a slight increase in streptavidin reactivity post tumour challenge (see FIG. 5C).

Specifically, the streptavidin (50 µg) only vaccine group showed an upregulation of cytokines, IL-1β, IL-13, TNF-α, MIP-3a and VEGF, while M-CSF was down regulated in this group compared to controls. (Table 1). In cured rats from Vaccine (50) group (n=2), TNF-α was upregulated when compared to controls at endpoint (Table 1), while IFN-γ and MIP-3a were down regulated compared to controls. Conversely, rats from this same group not in remission had endpoint levels that were significantly lower than controls (P<0.05, Table 1). The cytokine ICAM was significantly down regulated in the vaccine (50) compared to controls (FIG. 6E). CINC-1 was not significantly elevated in any group (FIG. 7B).

Overall, cytokine analysis on serum samples collected at day 21 of the vaccine components trials showed no significant difference between the control groups and the reduced tumour protein (R-lysate) group (FIGS. 6D and E, 7B and Table 1).

In general, C reactive protein levels increased in all groups post tumour challenge but there was no significant difference in levels between groups (FIG. 7A). TNF-α levels in vaccine treated rats were significantly increased only in the vaccine treated group 3 weeks post tumour challenge (FIG. 6D).

TABLE 1

Circulating cytokine response at endpoint relative to control vaccinated rats. The Vaccine (50) group was further divided into 2 groups, those surviving > 100 days, considered in remission; and the remainder.

| Group | N | Survival Mean ± SD | Cytokine response relative to control P < 0.05 Increased | Decreased |
|---|---|---|---|---|
| Control | 5 | 38.4 ± 3.0 | — | — |
| R-Lysate | 6 | 43.0 ± 2.7 | NSD | NSD |
| Streptavidin | 6 | 51.3 ± 11.3 | IL-1β, IL-13, MIP-3A, VEGF | M-CSF |
| Vaccine (50) | 6 | 76.8 ± 18.6 | | |
| | (4) | Died < 77 days | IL-1α, IFN-γ, MIP-3A | TNF-α |
| | (2) | Survived > 100 days | TNF-α | IFN-γ, MIP-3A |
| Vaccine (100) | 3 | 43.5 ± 6.1 | NSD | NSD |

SD: Standard deviation; N: number in each cohort; NSD: No significant differences.
Cytokines measured that did not show significant differences in any groups: IL-2, IL-4, IL-5, IL-6, IL-7, IL-10, IL-12, IL-17, IL-18, EPO, G-CSF, GRO-KC, MIP-1A, Rantes.

Figure 8:
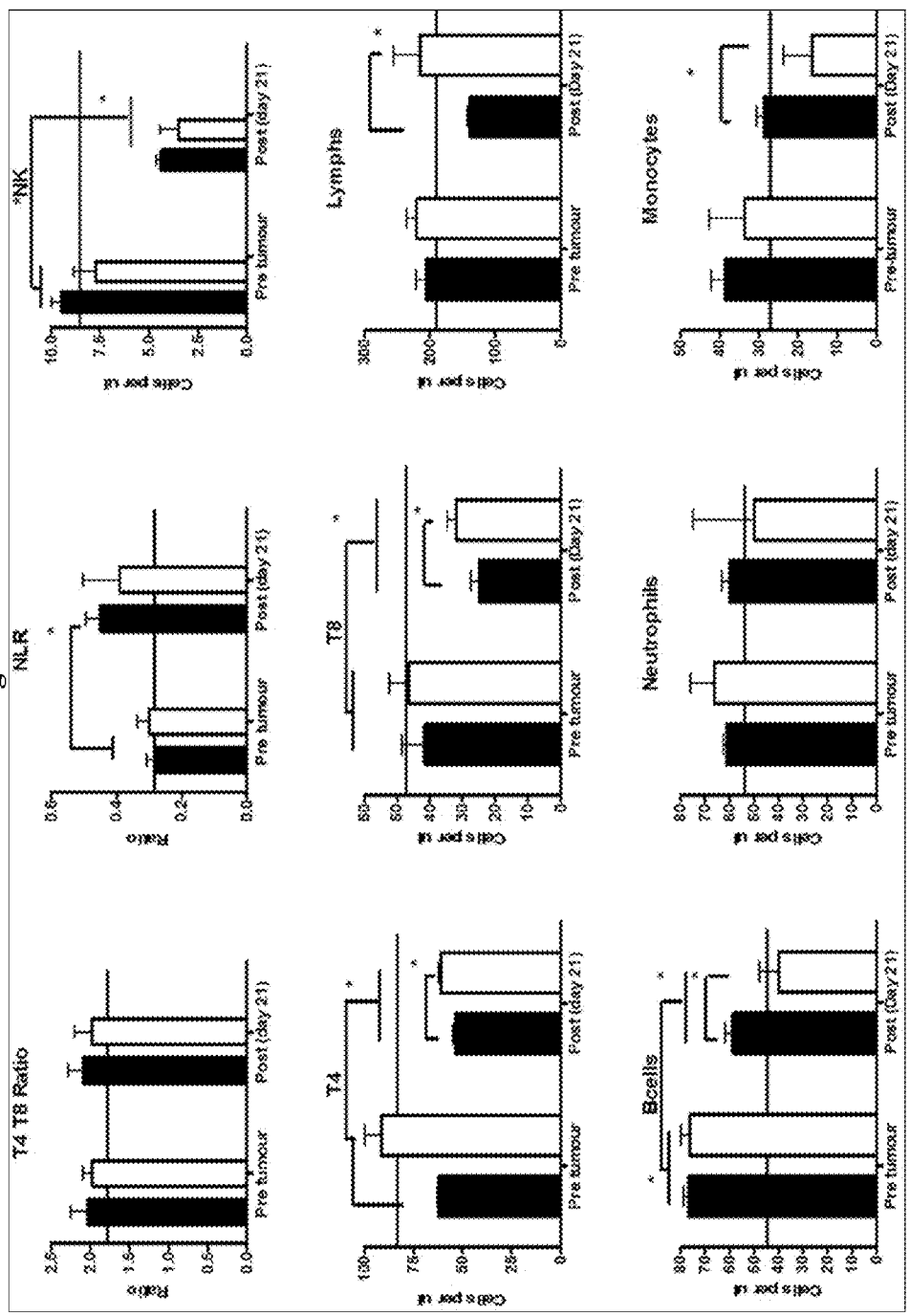
FIG. 8 shows the results from a flow cytometric blood assay performed with vaccinated and unvaccinated rats. Blood analysis on control rats (Black bars; adjuvant only n=6) and vaccine treated rats (white bar n=6): Pre tumour sample point was taken after vaccination and prior to tumour challenge. Post tumour sampling was performed 21 days after tumour challenge. All rats were bled prior to any treatment to provide baseline control levels of all cell types (Black line, n=12).

A multicolour flow cytometry assay was developed to analyse multiple peripheral blood cell types in a small peripheral blood sample. The assay detected the number of NK, CD4, CD8, B Cell, Lymphocytes, monocytes and neutrophils per microliter of blood. Adjuvant only and reduced tumour protein+streptavidin vaccine treated rats had their blood tested one week after secondary vaccination (Pre tumour) and 3 weeks post tumour challenge (Post) (see FIG. 8). Significant differences in NK cell levels were seen pre- and post-tumour challenge in both adjuvant treated and vaccine treated groups. CD4 cells were significantly increased in vaccine treated rats both pre- and post-tumour challenge compared to control, but both groups CD4 levels dropped significantly post-tumour challenge (FIG. 8). CD8 levels were reduced in both groups 21 days post tumour challenge however were they significantly reduced in the adjuvant only group (FIG. 8). B cells showed elevation compared to base line levels in both groups pre tumour challenge, but dropped significantly post tumour challenge. B cell levels returned to normal baseline levels in vaccine treated rats (day 21) indicating that the response to the tumour may have been cell mediated. Vaccination caused a spike in monocyte levels, which again decreased to normal levels in vaccine treated rats but remained elevated in control groups (FIG. 8). Neutrophil to lymphocyte ratio (NLR) was at baseline levels after vaccination but increased significantly in controls after tumour challenge, but not in vaccine treated rats.

Example 3

Autologous Vaccine Preparation

Materials and Methods
Preparation of Solubilized Biological Samples
Fresh, healthy pieces of surgically removed tumour tissue (0.1 g of each) were homogenised in buffer containing 1% SDS (v/w), 0.05M Tris, 0.15M NaCl, pH 7.6 and then clarified by centrifugation. For every 0.1 g of tumour, 4 ml of buffer was added.

1 ml fractions of tumour protein extract were reduced for 1 hr with 20 mM TCEP or 50 mM DTT in the 1% SDS buffer. 150 µg of streptavidin was then added to each, before incubating for 2 hrs with gentle mixing.
Vaccine Preparation
After incubation the tumour protein-streptavidin mixtures were then precipitated overnight with 5 to 10 volumes of ice cold acetone at −20° C. These mixtures were then centrifuged at 10,000×g for 30 min, before decanting the acetone and allowing the pellets to air-dry.

Figure 9:
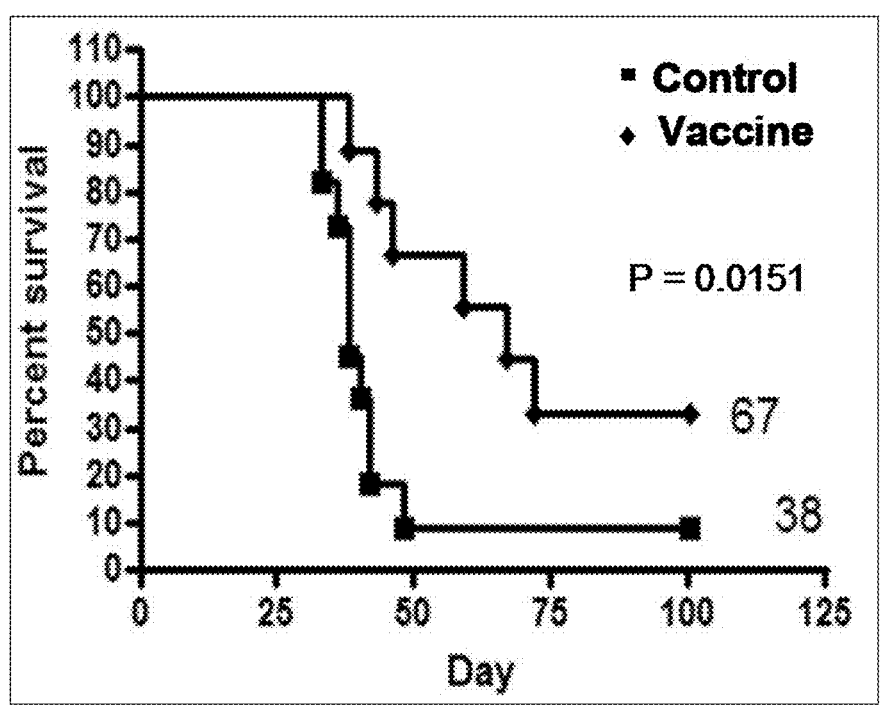
FIG. 9 shows the results achieved for a rat vaccine trial using autologous vaccines prepared with SDS extracted tumour proteins, a reducing agent and streptavidin, when compared with unvaccinated subjects.
Figure 10:
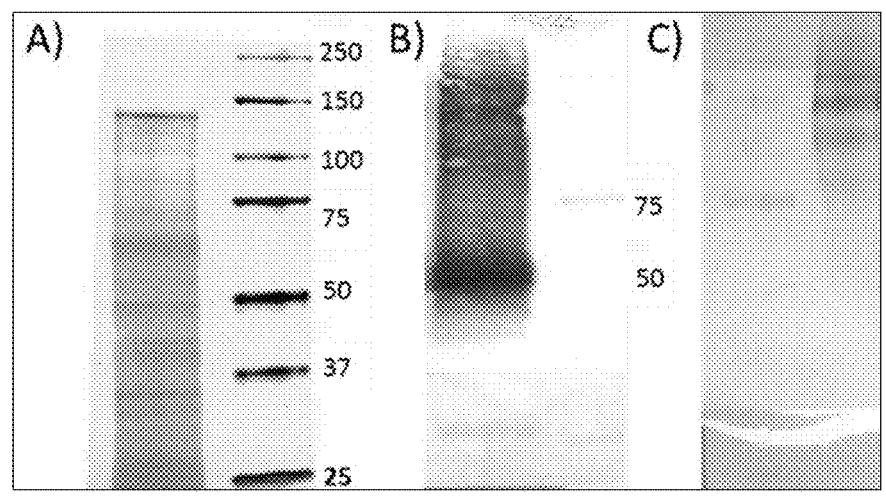
FIG. 10 shows a protein profile of a dog autologous vaccine. A) A silver stained SDS-PAGE gel of a typical dog personalised autologous vaccine. B) Streptavidin binding in vaccine. C) Biotin binding in the dog vaccine.

The dry pellets were resuspended in 600 µl of sterile PBS and mixed with 600 µl FIA and emulsified using a 19 G needle. The vaccine preparations were divided into three equal doses and subjects vaccinated subcutaneously with single doses at 0 and 3 weeks, followed by assessment of survival in comparison with control, unvaccinated subjects.
Results
The vaccinated subjects showed an increased mean length of survival of 67 days, while the control group demonstrated a mean length of survival of 38 days (FIG. 9).

Example 4

Dog Safety Trial with Autologous Vaccine

Materials and Methods
Fresh tumour samples comprising cancer cells were obtained by either biopsy of tumour or complete removal of the tumour. Tumour samples were frozen at −20° C. until processing. On day of processing the tumour sample was weighed. For every 0.1 gram of tumour 4 mls of buffer containing of 1% SDS (v/w), 0.05M Tris, 0.15M NaCl, pH 7.6 was added, in addition to a protease inhibitor (Roche). The tissue samples were then homogenised and filtered through a sieve to remove larger fibrous material.

The resulting lysate was centrifuged at 10,000 rpm for 15 min and the soluble fraction retained. TCEP was added to give a final concentration of 20 mM TCEP and the sample then incubated for 1 h at room temperature before adding 100 µl of Biotin-NHS (1 mg/ml concentration). After incubation at room temperature for 2 hours, 100 µl of 1 mg/ml streptavidin (Sigma) was then added and the mixture incubated for 2 h.

The lysate was then precipitated by the addition of at least 5 volumes of cold acetone and an overnight incubation at −20° C. The precipitate was harvested by centrifugation at 10,000 rpm for 30 min at 4° C., the supernatant decanted and the pellet allowed to air-dry until the acetone had evaporated.

The pellet was then resuspended in 600 µl of PBS and split into 2×0.3 ml aliquots (for 2 vaccinations), before freezing at −20° C.

On the day of vaccination, one aliquot of vaccine was thawed and mixed with an equal volume of FIA, and administered subcutaneously (0.6 ml). This was repeated 3 weeks later.

Results

The autologous vaccine prepared for the dog safety trial was analysed by SDS-PAGE and western blot (see FIG. 8).

Figure 11:
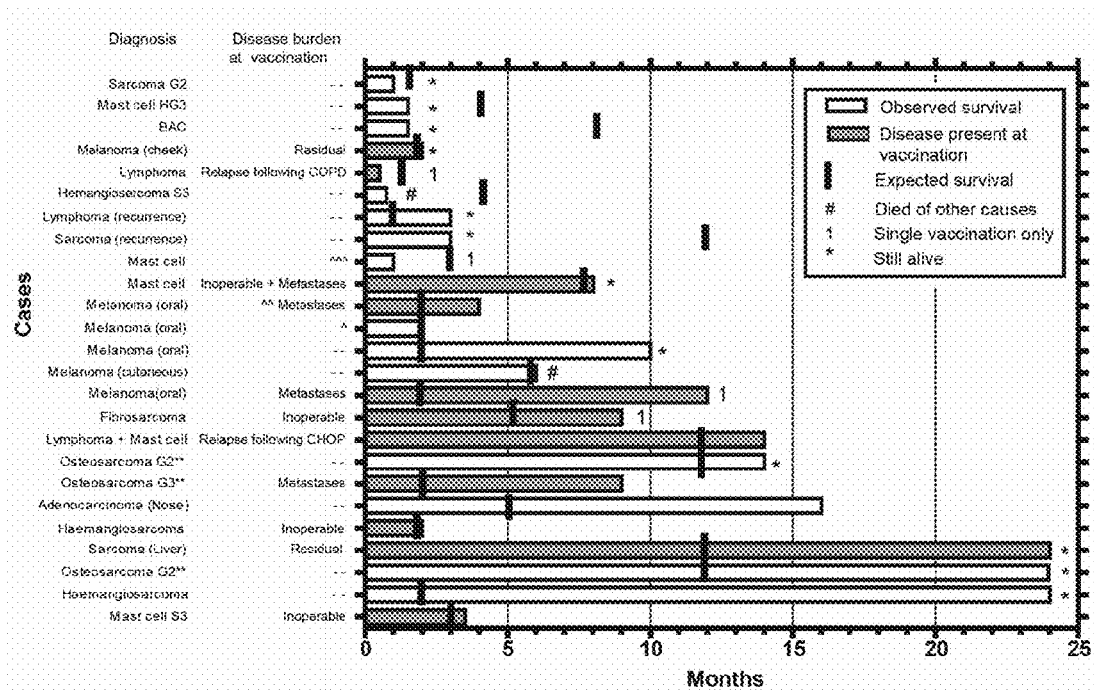
FIG. 11: Phase I canine clinical trial of the autologous vaccine demonstrates safety and efficacy (n=25). Individual cases (y axis) are described (diagnosis and disease burden at time of vaccination) and plotted against survival time in months (x axis). The expected survival times were taken from patient notes or the British Small Animal Vet Association Manual of Canine and Feline Oncology (2011). ** dogs received carboplatin with vaccine; ^, ^^, ^^^-vaccination given 3, 4, 8 months (respectively) after resection; BAC: Broncoalvelolar carcinoma; G: grade; HG: high grade; S: stage; COPD: Chemotherapy of Mitozantrone, Doxorubicin, Vincristine and Cyclophosphamide; CHOP: Chemotherapy of Cyclophosphamide, Hydroxydaunorubicin (doxorubicin), Oncovin (vincristine) and Prednisone.

The dog safety trial was commenced in March 2011. Despite many of the animals entering the trial in ill-health, there were no adverse reactions to the vaccine other than a localised inflammation at the vaccination site. The results of the trial to approximately April 2013 are presented in Table 2 in terms of individual animals. The results of the trial to approximately August 2013 are shown in FIG. 11 with results grouped on the basis of cancer type. The vaccine has proven to be safe to deliver which on a wide range of chemotherapies, steroids and other drugs with no adverse reactions (Table 2). It has also been demonstrated to be safe in different breeds and over 10 different tumour types.

TABLE 2

Survival in Dog Safety trial with Autologous Vaccine.

| AGE/SEX | BREED | Tumour Type/Grade | Mitotic index | Expected survival | Actual survival | Other Medications | Comments |
|---|---|---|---|---|---|---|---|
| 12 yo Male | Staffodshire Bull Terrier | Mast cell stage 3 | 18/10 | 3-4 m | 3.5 m | Prednisone | Steroid treatment would nullify effect of vaccine |
| 9 yo Male | Staffodshire Bull terrior | Haemangio-sarcoma | 6/10 | | 23 months (ongoing) | | No reoccurance of haemagiosarcoma, but did present with mast cell tumour 11 months after vaccinations. |
| 12 yo female | Rottweiler | Ostero-Sarcoma grade 2 (amputation) | | 12 months | 18 months (ongoing) | Carboplatin prior to vaccine | No metastatic disease or reoccurrence |
| 13 yo female | Kelpie | Sarcoma (liver) | | | 24 months (ongoing) | | No reoccurrence or metastatic disease |
| 14 yo male | Labrador | Haemangio-sarcoma | | | 8 weeks | | Inoperable tumour. Vaccine made from small sample. |
| 12 yo female | | Adeno-Carcinoma (nose) | | | | | |
| 10 yo female | German Spitz | Osteosarcoma grade 3 (amputation) Chest mets | | <3 months (metastatic disease) | 9 months | Carboplatin and vaccinations | Combined carboplatin and vaccine safe. Survived longer than expected-chest mets. |
| 11 yo male | Alaskan malamute | Osteosacroma grade 2 (amputation) | | | 12 months (ongoing) | Carboplatin and vaccinations | No reoccurrence or metastatic disease |
| Max | | | | | | CHOP | CHOP relapse: Vaccine made |
| Billy Leonard ACE | Labrador | (Biopsy) | | | | | |
| 7 yo female | Crossbreed | Soft tissue sarcoma | | | | | Vaccine after radiation |
| 19 yo | Jack Russell | Melanoma (oral mass) | | | | | Progressive disease |
| 6 yo | American staffordshire | Melanoma | | | | | |
| 16 yo | Silky terrier | Melanoma (oral) | | | | | |
| Ralph | | Melanoma | | | | | |
| 14 yo | Golden Retriever | | | | | | |
| 5 yo | Cavadoodle | | | | | | |
| 3 yo | Sharpei | | | | | | |
| 12 yo | Rottweiler | | | | | | |

TABLE 2-continued

Survival in Dog Safety trial with Autologous Vaccine.

| AGE/SEX | BREED | Tumour Type/Grade | Mitotic index | Expected survival | Actual survival | Other Medications | Comments |
|---|---|---|---|---|---|---|---|
| 13 yo Male | German Shepherd | Connective tissue sarcoma (re-occuting) | 4/10 | | 3 months (ongoing) | Oral carboplatin (prior to vaccine) | No reoccurrence or metastatic disease |
| 11 yo male | English Setter | Lymphoma (re-occuring) | | | 3 months (on going) | Vincrsitine injections and cyclophosphamiide | No reoccurrence or metastatic disease |
| 13 yo female | Labrador | Haemangio-sarcoma (stage 3) spleen | | | 3 weeks | | Complete removal of spleen. Died of internal bleeding before finishing vaccine course |
| 6 yo male | Rottweiller cross | Malignant Lymphoma | 18/10 | | 2 weeks | COPD: Doxorubicin Vincristine Cyclophosphamide Mitrozantrone | Pretreated with COPD protocol, however had relapsed. Vaccinated as last resort. |
| SASH | Labrador | Metastatic Lymph node | | | | | |
| 15 yo Female | Golden Retriever | Malignant Melanoma (cheek) | 2/10 | | 2 months | | No reoccurrence or metastatic disease |
| 8 yo female | Miniature Schauzer | Bronchoalveolar carcinoma | 15/10 | | 1.5 months | | No reoccurrence or metastatic disease |
| 13 yo female | Kelpie cross | Mast cell tumour High grade 3 | | <4 months predicted | 1.5 months | | No reoccurrence or metastatic disease |
| 10 yo female | Siberian Husky | Connective tissue sarcoma (grade 2) | 5/10 | | 4 weeks | | No reoccurrence or metastatic disease |

The tumour types and survival data for this trial are also shown in FIG. 11. Expected survival times were taken from either individual oncology reports or published literature and were based on surgery alone or standard of care for the tumour type.

Of the 25 dogs included in this study 10 had residual tumour after either biopsy, partial resection or metastatic disease. Sixty percent of these (6/10) survived longer than expected.

Of the other 15 which had complete tumour resection, 40% (6/15) survived longer than expected and a further 5 are still at a stage where it is too early to see if they have benefited from the vaccine. A further 9 dogs had vaccines made for them however died of other complications prior to receiving a dose or the owner decided not to proceed.

Ninety percent (16/18) of dogs receiving 2 vaccinations exceeded their expected survival time by 2 weeks to 22 months at the census date. None of these dogs died prior to their expected survival time (excluding unrelated causes). A further 4 dogs are alive but have not reached their expected survival. No cases of anaphylaxis occurred and the only side effect recorded was a subcutaneous nodule at the vaccination site which resolved over time. Some of the dogs enrolled in this safety trial were also receiving or had received other therapies including chemotherapeutics (e.g. Cisplatin, Carboplatin, Vincristine, Doxirubicin and cyclophosphomide) and steroids (Prednisone) and other drugs (Ciproflaxin and Allopurinol). These results demonstrate the safety and efficacy of the vaccine in a clinical setting. The fast turn, around time from tumour resection or biopsy also means minimal lag time to treatment which is also important in a clinical setting.

Example 5

Treatment of a Human Patient with a Cancer Vaccine

Materials and Methods
Preparation of the Vaccine

A 63 year-old male with advanced colorectal cancer with metastasis to the liver, lungs and spine underwent surgery to remove a tumor in the spine. The tumor (0.5 g) was used to prepare the vaccine. The tumor vaccine was prepared as described in Example 4.

Vaccination

The vaccine was administered by subcutaneous injection in to the stomach. The second vaccine was administered two weeks later.

Post Vaccination Monitoring

Blood was collected 18 days after the second vaccination and analysed by flow cytometry. Results are presented in Table 3.

TABLE 3

Blood analysis post-vaccination and in controls

| Cells per ul of whole blood | Cancer patient | Normal 1 (cw) | Normal 2 (AH) |
|---|---|---|---|
| White cells 4500-10,500 | 5200 | 4200 | 6000 |
| Lymphs 1000-4000 | 1752 | 1900 | 2600 |
| T cell (CD3 + 16 − 19−) 700-2100 | 1111 | 1290 | 1810 |
| T4 Cell (CD3 + 4 + 8−) 400-1400 | 636 | 747 | 1250 |
| T8 Cell (CD3 + 8 + 4−) 200-900 | 454 | 480 | 454 |
| T-Regs(CD3 + 4 + 25 + 127−) | 63 (9.1% of his CD4s) | 58 | 85 |
| B Cell (CD19 + 3 − 16−) 50-500 | 129 | 270 | 470 |
| NK cell (CD2 − 19 − 16+) 50-600 | 477 | 56 | 128 |

TABLE 3-continued

Blood analysis post-vaccination and in controls

| Cells per ul of whole blood | Cancer patient | Normal 1 (cw) | Normal 2 (AH) |
|---|---|---|---|
| Neutrophils 2000-7500 | 2970 | 1670 | 2850 |
| Monocytes | 177 | 300 | 400 |
| NLR | 1.7 | 1.1 | 0.9 |
| CD4/CD8 ratio | 1.4 | 1.56 | 2.75 |

The natural killer (NK) cell count is significantly raised, indicating an immunological response. The clinical oncologist who was managing the patient reported that the results from the blood analysis indicated that the vaccine was having an effect and decided to halt a planned chemotherapy treatment.

Discussion Pertaining to Cancer Vaccine

This study demonstrated that vaccines developed using the methods described herein can stimulate the immune system to recognise and either slow tumour growth or induce tumour rejection. Prophylactic allogenic vaccination of the 9L glioma rat model doubled survival in 100% of rats and led to remission in 33% of these. Rechallenging rats in remission demonstrated 100% tumour rejection. Autologous vaccination in the clinical setting of dogs with advanced cancer demonstrated safety as well as "real world" applicability of the rapid production method with initial evidence of efficacy.

In the experiments described herein streptavidin is effective at selecting tumour proteins and stimulating the immune system. The binding of streptavidin to proteins is through its RYDS sequence which mimics the RGD cell adhesion domain of fibronectin. There are over 60 integral membrane proteins that contain an RGD sequence and could potentially bind streptavidin. Many of these proteins such as integrins, VEGF-A, angiopoientin, osteopoientin and fibronectin have been shown to have a role in cancer development.

However vaccination with strepavidin alone did not induce remission and the inventors combined this with soluble tumour proteins reduced under denaturing conditions to prevent refolding. While the final precipitation step has been used before as a potent way to present antigens with low immunogenicity, utilizing soluble proteins as described herein sets the process and vaccines apart as most other vaccines are derived from ethanol fixed or irradiated whole cells. In specific embodiments described herein the soluble proteins are then reduced with TCEP which permanently breaks disulphide bonds and provides a stable environment for proteins.

A combination exemplified herein (streptavidin plus reduced soluble proteins; Vaccine (50) was associated with tumour remission and rejection in the 9L glioma model. Other studies have successfully used different therapies such as suicide gene transfer or nanoparticles to slow tumour growth, but to the knowledge of the inventors this is the first report of inducing complete remission in this aggressive model. Of note, while the 9 L glioma model has been reported to be immunogenic, the inventors observed 100% engraftment with no spontaneous remissions in keeping with other reports using this cell line.

Results presented herein suggest that the vaccine modulates the immune response from a predominantly antibody response (to streptavidin) to a cell mediated response (requiring the addition of the reduced tumour lysate). B-cells were elevated in both vaccine and control following vaccination, demonstrating that the adjuvant FIA stimulates an increase in peripheral B cells as previously described. However by 21 days post engraftment, B-cell counts of vaccine treated rats had returned to normal levels indicating again a switch to a cell mediated response to the tumour. While CD8+ T cell numbers (also referred to herein as T8) dropped significantly 21 days post tumour challenge in both groups, vaccine treated rats CD8 levels were significantly higher than control at day 21. This suggests that lymphocyte production is stimulated by the vaccine and aids in the extended survival. In support of the importance of maintaining normal lymphocyte levels, low levels in cancer patients are reported to be indicative of poorer prognosis and higher tumour grade. Melanoma and colorectal patients with a higher level of tumour infiltrating lymphocyte (CTL's) also have a better prognosis.

The key cytokine response observed was up regulation of TNF-α which is known to have an anti-tumour effect and causes cancer cell apoptosis. While streptavidin only vaccinated rats showed increased survival they did not show the corresponding up regulation of TNF-α seen in vaccine treated rats. ICAM1 a cytokine implicated in tumour growth and metastasis was also down regulated only in vaccine treated rats.

Cytokine analysis also identified differences in the levels of IL-4 and INF-γ between vaccine treated and control rats. IL-4 which has been shown to modulate tumour progression and metastasis was decreased in vaccine treated rats. Vaccine treated rats also showed a significant increase in INF-γ which is a critical immune system component of the anti-tumour response. INF-γ together with lymphocytes not only provide protection against tumour development but also assist to sculpt the immunogenic phenotype of tumours for presentation as a "cancer immunoediting" process. Taken together the cytokine results suggest that the vaccine initiates a specific and effective immune anti-tumour response.

While rat models are useful for the initial evaluation of vaccine preparations, dogs provide a clinical presentation and scenario to match that of humans in terms of presentation and time to progression. The dogs were assessed as a Phase I safety trial with no adverse reactions observed when the vaccine was administered alone or in combination with a variety of other medications. These results confirm the safety of the autologous vaccine protocol.

This study also provided initial evidence for the efficacy of the vaccine in this clinical setting with canine patients presenting with varying degrees of disease (operable to metastatic) and tumour types. Dogs with residual or metastatic disease often survived longer than expected indicating vaccination can slow tumour growth. The ability to produce an autologous vaccine in several days highlights its applicability to clinical situations with a lag time of only a few days between surgery and treatment. Furthermore, fresh tumour samples once frozen can be stored indefinitely until the vaccine is required if using in an adjunct setting. The examples provided herein also provide initial clinical evidence for the efficacy of the vaccine in the treatment of a human patient with cancer.

The invention described herein provides a unique vaccine process for making autologous or allogeneic tumour vaccines with evidence of both slowed growth and remission. In specific embodiments exemplified herein the use of streptavidin as an immune stimulant with reduced tumour proteins is effective, safe and well tolerated in rodents and canine patients, thereby illustrating that the invention provides a novel platform for the development of improved cancer vaccines.

Example 6

Treatment of Rats with a Combination of Adipose Derived Rat Cells and a Cancer Vaccine Prior to Induction of Tumours Materials and Methods
Processing of Adipose Tissue A 10 g sample of adipose tissue was collected from a rat. The adipose tissue was rinsed with saline and then minced finely using scissors and mixed with 20 mls of Dulbecco's Modified Eagle's Medium (DMEM, Sigma). Collagenase (Sigma) was added to a final concentration of 0.05% and the sample was incubated at 37° C. for 30 minutes. During the incubation the sample was gently inverted by hand every 15 minutes.

Following collagenase treatment the sample was aseptically filtered through a stainless steel mesh (700 µm pore size), transferred to a 50 ml centrifuge tube and centrifuged at 500 g for 15 minutes. The floating cells and the supernatant were discarded and the pelleted cells were gently mixed with a pasteur pipette and transferred to a 15 ml centrifuge tube.

The cells were then washed in DMEM to remove collagenase. DMEM was added to a final volume of 14 mls and the sample centrifuged at 500 g for 10 minutes. The supernatant was discarded and the pelleted stromal vascular fraction (SVF) cells were gently resuspended in 4 mls of DMEM and mixed with a pasteur pipette.

Expansion of Cells

Aliquots (0.5 mls) of the cell suspension were transferred to tissue culture flasks containing DMEM plus 20% foetal calf serum and incubated in a CO2 incubator at 37° C. until a confluent cell monolayer was present (7 to 10 days). Cells were stripped with 3 mls of TrypLE Express (Invitrogen), decanted into 50 ml centrifuge tubes and centrifuged at 500×g for 10 minutes.

Cryopreservation of Cells

The pelleted cell samples were resuspended in either foetal calf serum. The cell suspensions were then transferred to cryovials in 2 ml aliquots.

DMSO was added to each cryovial to produce a concentration of 10% and the cryovials were frozen in a Mr Frosty slow freezing device (Invitrogen) in a −80° C. freezer for 24 hours and then transferred to a liquid nitrogen dewar for long term storage.

Administration of the Cancer Vaccine

A cancer vaccine was prepared as described herein. The vaccine was mixed with Freunds Incomplete Adjuvant (FIA) and administered intra peritoneally in to two groups of 3 rats. The vaccine was administered again 3 weeks later. A further 3 rats were used as a control group and were vaccinated with just the FIA.

Administration of Cells

Vials of cells were removed from liquid nitrogen and allowed to thaw at room temperature. Approximately $1\times10^6$ stem cells were administered by subcutaneous injection to one group of 3 rats at the same time and to the same site as the vaccine.

Challenge with Tumours

After the final vaccination all three groups rats were challenged with a 9L tumour in the flank and the growth of the flank tumours were monitored and the survival rate of the rats recorded. The study was completed at 100 days and any rats still alive were given a survival score of 100 days.

Results

Figure 12:
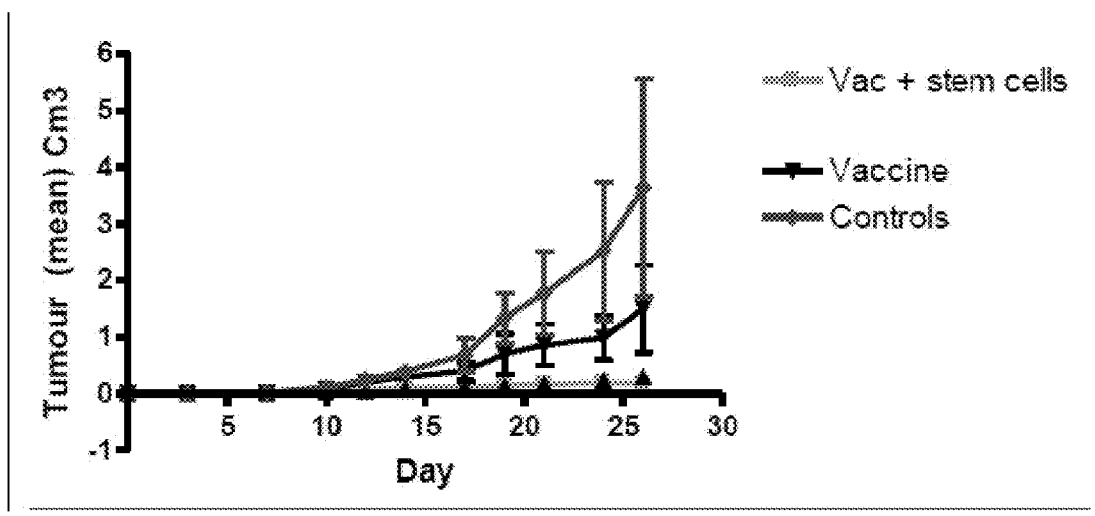
FIG. 12 shows the average tumour size of the control rats, the vaccinated rats and the rats that received the vaccine plus the adipose derived cells. The rats that received the vaccine plus the adipose derived cells showed a dramatic reduction in tumour size compared to the controls and the rats that received just the vaccination.
Figure 13:
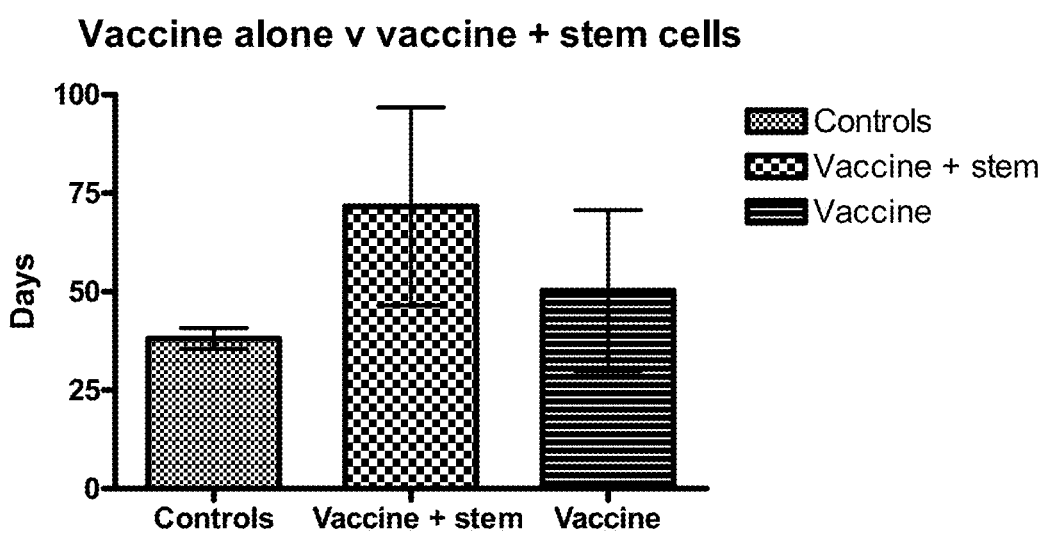
FIG. 13 shows the average survival times for the control rats, the vaccinated rats and the rats that received the vaccine plus the adipose derived cells.

The results of the trial are summarised in FIGS. 12 and 13. The group that received stem cells in combination with the vaccine showed almost complete retardation of tumour growth. The mean survival time of the group that received stem cells in combination with the vaccine was considerably higher than the vaccine alone group as well as the control group.

Example 7

Treatment of Rats with a Combination of Adipose Derived Canine Cells and a Cancer Vaccine Prior to Induction of Tumours Materials and Methods
Preparation of Adipose Derived Cells A 10 gram sample of adipose tissue was collected from a female Labrador during a routine desex procedure. The adipose tissue was processed to produce a suspension of stromal vascular fraction cells as detailed in Example 6.

Expansion of Cells

Aliquots (0.5 mls) of the stromal vascular cell suspension were transferred to tissue culture flasks containing DMEM plus 20% foetal calf serum and incubated in a CO2 incubator at 37° C. until a confluent cell monolayer was present (7 to 10 days). Cells were stripped with 3 mls of TrypLE Express (Invitrogen), decanted into 50 ml centrifuge tubes and centrifuged at 500×g for 10 minutes. Half of the cells were cryogenically stored at this point to produce a minimally passaged cell suspension. The cells were frozen in cryogenic vials as described in Example 6. These vials were labelled as D0.

The remaining cells were cultured more extensively by continuing to passage the cells until they reached approximately 10 cumulative cell doublings. The cells were then stripped and frozen in cryogenic vials as described in Example 6. These vials were labelled as D4.

Administration of the Cancer Vaccine

A cancer vaccine was prepared as described herein. Briefly stated, vaccine was made by processing tumours from 6 donor rats. Tumours were homogenised in 1% SDS, 0.05M Tris, 0.15M NaCl ph 7.6 buffer and centrifuged at 10,000×g for 30 mins to pellet insoluble material. The soluble lysate was collected. A 1 ml volume of this lysate was then used to make vaccine for 3 rats. The 1 ml of lysate was treated with 0.0057 g of TCEP for a final concentration of 20 mM for 1 hour. Then 150 µg of Biotin-NHS (Thermo) was added to the reduced lysate for 2 hours followed by 150 µg of recombinant streptavidin (genscript). After incubation for 2 hours the labelled/reduced lysate was precipitated overnight at −20° C. with 20 ml of cold acetone. The next day the sample was centrifuged at 10,000×g for 30 mins to pellet the sample. The acetone was tipped off and the residual acetone was allowed to evaporate off. The vaccine pellet was then resuspended in 600 µl of sterile PBS. To make up the final vaccine for administration 600 µl of Freunds incomplete adjuvant was added to the 600 µl vaccine and mixed into a white thick paste. Each rat was then administered approximately 300 µl of vaccine at the back of the neck.

The vaccine was administered again 3 weeks later. A further 3 rats were used as a control group and were vaccinated with just the Freunds incomplete adjuvant.

Administration of Cells

Vials of cells were removed from liquid nitrogen and allowed to thaw at room temperature.

One group of 3 rats received 300 µl (3×10⁶ cells) of D0 cells next to the vaccination site at the same time as the vaccination. A repeat injection of D0 cells (3×10⁶ cells) was administered with the second vaccination at the 3-week time point.

A second group of 3 rats received 300 µl (3×10⁶ cells) of D4 cells next to the vaccination site at the same time as the vaccination. A repeat injection of D4 cells (3×10⁶ cells) was administered with the second vaccination at the 3-week time point.

Challenge with Tumours

After the final vaccination D0 and D4 rats and the control group of rats were challenged with a 9L tumour in the flank. The growth of the flank tumours was monitored and the survival rate of the rats recorded. The study was completed at 100 days and any rats still alive were given a survival score of 100 days.

Results

Figure 14:
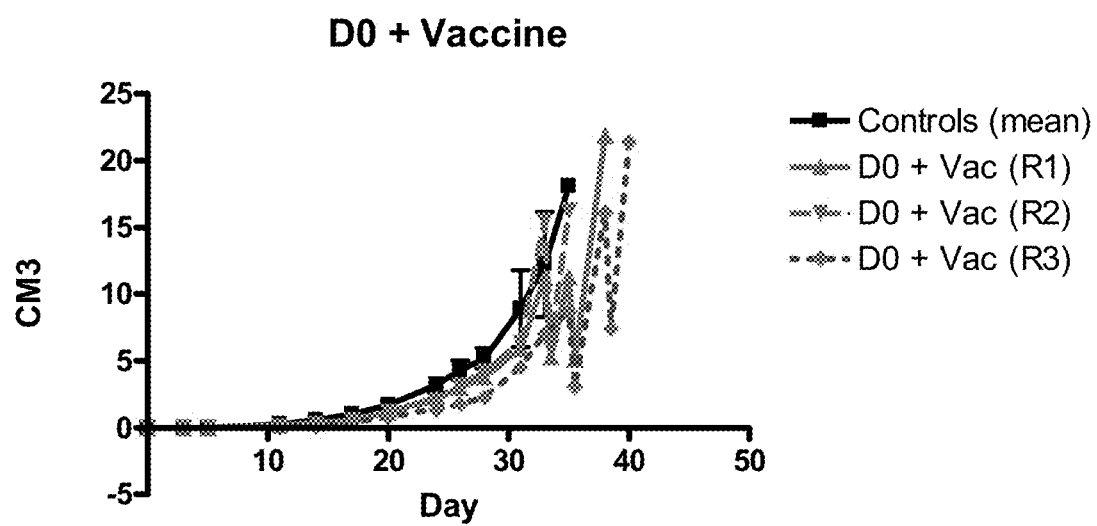
FIG. 14 shows average tumour size for the control rats and the tumour size for the individual rats for the rats that received the vaccination and the D0 canine adipose derived cells.
Figure 15:
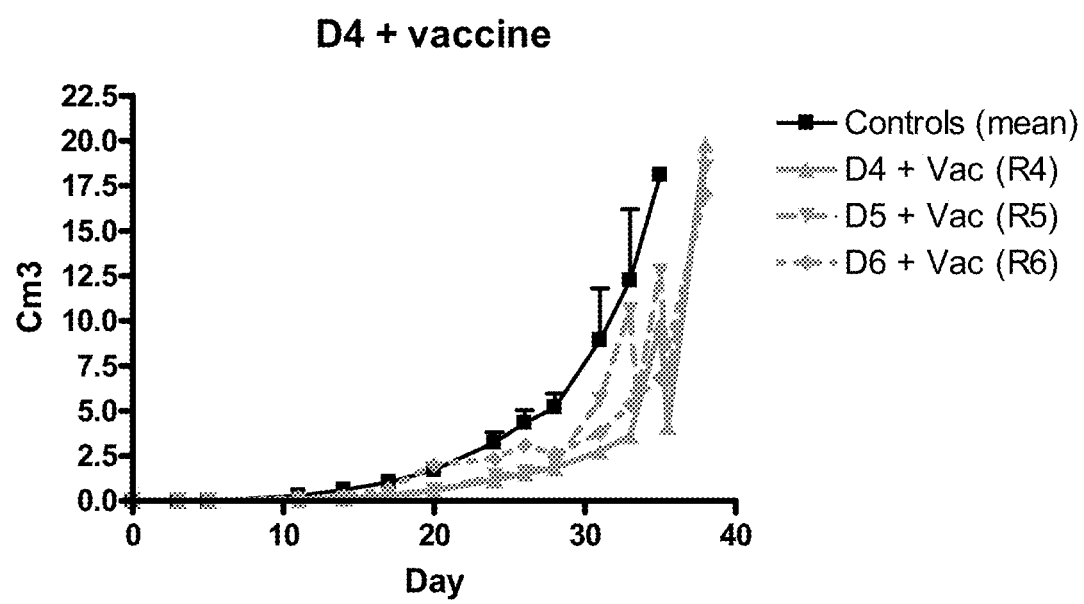
FIG. 15 shows average tumour size for the control rats and the tumour size for the individual rats for the rats that received the vaccination and the D4 canine adipose derived cells.

The results of the trial are summarised in FIGS. 14 and 15. Both the D0 group of rats and the D4 group of rats survived longer than the control rats. The D4 group of rats survived longer on average than the D0 group of rats.

Example 8

Therapeutic Treatment of Rats with a Combination of Adipose Derived Canine Cells and a Cancer Vaccine Materials and Methods
Induction of Tumours Two groups of 3 rats were challenged with a 9L tumour in the flank and the growth of the flank tumours were monitored and the survival rate of the rats recorded. The study was completed at 100 days and any rats still alive were given a survival score of 100 days.

Delivery of Vaccination and Cells

Once each rat had a palpable tumour (day 5) three of the rats were then administered with vaccine (prepared as detailed in Example 7). The rats also received 5×10⁵ canine D4 cells at the vaccine site and a further 5×10⁵ canine D4 cells next to the tumour. At day 26 the vaccination and the cell administration was repeated.

Results

Figure 16:
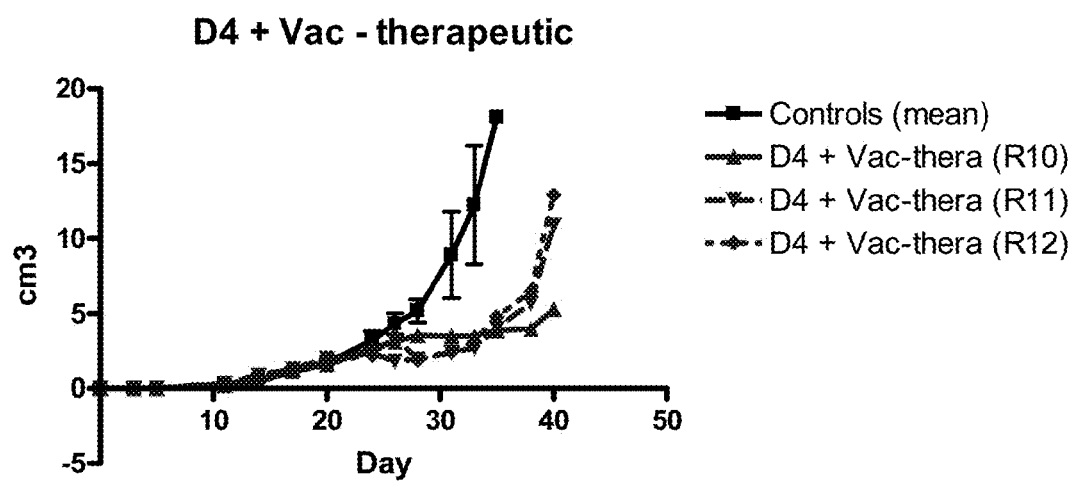
FIG. 16 shows average tumour size for the control rats and the tumour size for the individual rats for the rats that received the vaccination and the D4 canine adipose derived cells after induction of the tumour.

The results of the trial are summarised in FIG. 16. The tumour sizes in the treated rats were considerably reduced compared to the controls.

Example 9

Administration of Adipose Derived Equine Cells in Combination with a Strangles Vaccine Materials and Methods
Preparation of Equine Adipose Derived Cells Equine adipose tissue was collected from the tail base of a horse. The adipose tissue was processed as detailed in Example 6. Cells were cultured to passage one and frozen as detailed in Example 6. Cells were thawed at room temperature immediately before administration.

Delivery of Vaccination and Cells

Two four year old female horses were administered a commercial (Pfizer) vaccine for Strangles by intramuscular injection. Approximately 2×10⁶ adipose derived equine cells were administered at the same injection site. The injection of vaccine and the cells was repeated 3 weeks later.

Serology

Blood was collected prior to vaccination and at 1 week after the second vaccination. Serology was performed by IDEX Laboratories using an ELISA test.

Results

Both horses showed a baseline serology result prior to vaccination of weak positive at a 1 in 200 dilution.

After vaccination the horse that received the vaccination only showed a marginally increased serology result of weak positive at a 1 in 400 dilution. The horse that received the vaccination and the adipose derived cells showed a larger increase in the serology result to a moderate positive at a 1 in 800 dilution.

Example 10

Enhanced Antibody Response to Streptavidin

Immunization of Rats

Rats were immunized with a cancer vaccine and challenged with tumour cells as described in Example 6. The experiment comprised of three groups of three rats; a control group, a group that received the vaccine and a group that received the vaccine plus rat adipose derived stem cells. The stem cells were prepared and administered as described in Example 6.

Analysis of Serum

Serum was collected from the rats and analyzed by ELISA for antibodies to streptavidin. Streptavidin is a component of the cancer vaccine.

Results

Figure 17:
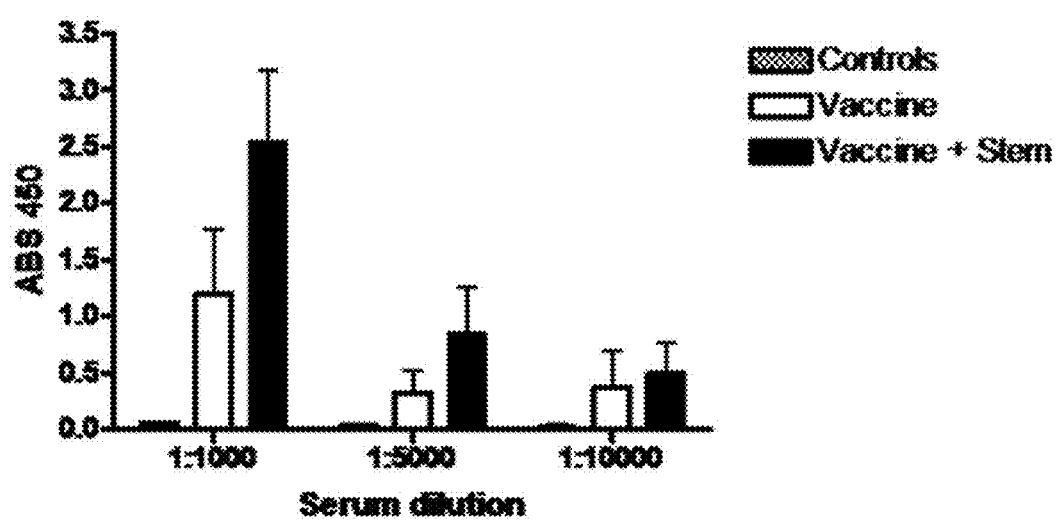
FIG. 17 shows antibody response to streptavidin in rats immunised with a cancer vaccine, with or without administration of adipose tissue-derived stem cells.

Both groups of rats that received the cancer vaccine developed antibodies to streptavidin. The group that received the cancer vaccine plus the stem cells showed a higher level of antibody response to streptavidin than the group that received just the cancer vaccine (FIG. 17).

We claim:

1. A method for producing a vaccine for the treatment or prevention of cancer, the method comprising exposing a biological sample comprising at least one cancer cell to an ionic detergent, a reducing agent, and a non-mammalian polypeptide capable of binding a mammalian protein, wherein the non-mammalian polypeptide is streptavidin, avidin or neutravidin, obtaining a solubilized biological sample comprising components from the cancer cell, and the non-mammalian polypeptide capable of binding a mammalian protein, and precipitating the solubilized biological sample comprising said components and said non-mammalian polypeptide or a soluble fraction of the solubilized biological sample comprising said components and said non-mammalian polypeptide with solvent to obtain the vaccine for the treatment or prevention of cancer.

2. The method of claim 1 wherein the biological sample is from a subject intended to receive the vaccine.

3. The method of claim 1 wherein the ionic detergent is selected from the group consisting of sodium-dodecyl-sulphate (SDS), 3-[(3-Cholamidopropyl)dimethylammonio]-1-propanesulfonate (CHAPS), lithium dodecylsulphate, sodium cholate, sodium lauroylsarcosine and cetyltrimethylammonium bromide (CTAB).

4. The method of claim 3 wherein the ionic detergent is SDS.

5. The method of claim 4 wherein the biological sample is exposed to SDS at a concentration of 0.5 to 1.5% (w/v).

6. The method of claim 1 wherein the reducing agent is selected from the group consisting of 2-mercaptoethanol, 2-mercaptoethanolamine, cysteine-HCl, dithiothreitol (DTT), tris(2-carboxyethyl)phosphine (TCEP), tributylphosphine (TBP) and iodoacetamide.

7. The method of claim 6 wherein the reducing agent is TCEP or DTT.

8. The method of claim 7 wherein the biological sample is exposed to TCEP or DTT at a concentration of 1 mM to 100 mM.

9. The method of claim 1, wherein the non-mammalian polypeptide is streptavidin.

10. The method of claim 1, wherein the method further comprises exposing said solubilized biological sample to biotin before exposing to said non-mammalian polypeptide capable of binding a mammalian protein.

11. The method of claim 1 wherein the method further comprises exposing the biological sample to an alkylating reagent.

12. The method of claim 1, wherein the method further comprises resuspension of the resulting precipitate in a suitable liquid.

13. The method of claim 1 wherein the solvent is a polar organic solvent.

14. The method of claim 13 wherein the polar organic solvent is selected from the group consisting of ethanol, methanol, acetone, isopropanol, propanol and dimethylformamide.

15. The method of claim 14 wherein the polar organic solvent is acetone.

16. A method for producing a vaccine for the treatment or prevention of cancer, the method comprising the steps of:
 a) exposing a biological sample comprising at least one cancer cell to an ionic detergent in a suitable liquid to produce a solubilized biological sample comprising soluble material and insoluble material;
 b) partitioning the soluble and insoluble material of the solubilized biological sample to produce a soluble fraction and an insoluble fraction;
 c) exposing the soluble fraction to a reducing agent;
 d) exposing the soluble fraction to a non-mammalian polypeptide capable of binding a mammalian protein to produce a mixture comprising said soluble fraction and said non-mammalian polypeptide, wherein the non-mammalian polypeptide is streptavidin, avidin or neutravidin;
 e) performing a solvent precipitation of the mixture; and
 f) resuspending the precipitate in a suitable liquid to obtain the vaccine for the treatment or prevention of cancer;
optionally further comprising, at any stage before step d), exposing the biological sample or soluble fraction to biotin.

17. A method for producing a vaccine for the treatment or prevention of cancer, the method comprising the steps of:
 a) exposing a biological sample comprising at least one cancer cell to an ionic detergent and a reducing agent in a suitable liquid to produce a solubilized biological sample comprising soluble material and insoluble material;
 b) partitioning the soluble and insoluble material of the solubilized biological sample to produce a soluble fraction and an insoluble fraction;
 c) exposing the soluble fraction to a non-mammalian polypeptide capable of binding a mammalian protein to produce a mixture comprising said soluble fraction and said non-mammalian polypeptide, wherein the non-mammalian polypeptide is streptavidin, avidin or neutravidin;
 d) performing a solvent precipitation of the mixture; and
 e) resuspending the precipitate in a suitable liquid to obtain the vaccine for the treatment or prevention of cancer;
optionally further comprising, at any stage before step c), exposing the biological sample or soluble fraction to biotin.

18. The method of claim 16, wherein the non-mammalian polypeptide is streptavidin or avidin.

19. The method of claim 16, wherein the method further comprises the step of exposing said soluble fraction to biotin at any stage prior to performing said solvent precipitation of the soluble fraction.

20. The method of claim 16, wherein the method further comprises the step of exposing said soluble fraction to an alkylating reagent at any stage prior to performing said solvent precipitation of the soluble fraction.

21. The method of claim 17, wherein the non-mammalian polypeptide is streptavidin or avidin.

22. The method of claim 17, wherein the method further comprises the step of exposing said soluble fraction to biotin at any stage prior to performing said solvent precipitation of the soluble fraction.

23. The method of claim 17, wherein the method further comprises the step of exposing said soluble fraction to an alkylating reagent at any stage prior to performing said solvent precipitation of the soluble fraction.

* * * * *